US011293928B2

(12) United States Patent
Reiter et al.

(10) Patent No.: US 11,293,928 B2
(45) Date of Patent: Apr. 5, 2022

(54) LABELLED COMPOUNDS AND METHODS FOR MASS SPECTROMETRY-BASED QUANTIFICATION

(71) Applicant: BiognoSYS AG, Schlieren (CH)

(72) Inventors: Lukas Reiter, Thalwil (CH); Susanne Leslie Müller, Zürich (CH)

(73) Assignee: BiognoSYS AG, Schlieren (CH)

( * ) Notice: Subject to any disclaimer, the term of this patent is extended or adjusted under 35 U.S.C. 154(b) by 261 days.

(21) Appl. No.: 16/327,182

(22) PCT Filed: Aug. 17, 2017

(86) PCT No.: PCT/EP2017/070823
§ 371 (c)(1),
(2) Date: Feb. 21, 2019

(87) PCT Pub. No.: WO2018/036897
PCT Pub. Date: Mar. 1, 2018

(65) Prior Publication Data
US 2019/0187152 A1    Jun. 20, 2019

(30) Foreign Application Priority Data

Aug. 22, 2016   (EP) ..................................... 16185189

(51) Int. Cl.
*G01N 33/68*   (2006.01)
(52) U.S. Cl.
CPC ..... *G01N 33/6848* (2013.01); *G01N 33/6842* (2013.01); *G01N 2440/20* (2013.01); *G01N 2440/38* (2013.01); *G01N 2560/00* (2013.01)

(58) Field of Classification Search
None
See application file for complete search history.

(56) References Cited

U.S. PATENT DOCUMENTS

2014/0248603 A1   9/2014  Eichmeyer et al.
2015/0330969 A1   11/2015 Kempa et al.

FOREIGN PATENT DOCUMENTS

EP         1 686 372 A1   8/2006
WO         03/046148 A2   6/2003
(Continued)

OTHER PUBLICATIONS

Chuh, K. N., et al. Chemical Methods for Encoding and Decoding of Posttranslational Modifications, Cell Chemical Biology, 23, 86-107 (Year: 2016).*

(Continued)

*Primary Examiner* — Xiaoyun R Xu
(74) *Attorney, Agent, or Firm* — Sughrue Mion, PLLC

(57) ABSTRACT

Methods for peptide and/or protein quantification by mass spectrometry using labeled peptides, wherein multiple labels lead to distinct fragments for the labeled peptides and their unlabeled variant, thus facilitating data analysis and enhancing the potential for quantification. Methods for selecting the label and label position are further given, as well as sets of labeled peptides resulting from or for use in the above-mentioned methods. The methods and substances are especially useful for data-independent or multiplexed parallel reaction monitoring proteomics applications involving peptide quantification.

13 Claims, 17 Drawing Sheets

(56) References Cited

FOREIGN PATENT DOCUMENTS

WO    2014/107573 A1    7/2014
WO    2014/184320 A1    11/2014

OTHER PUBLICATIONS

Kai Pong Law, et al., "Recent advances in mass spectrometry: data independent analysis and hyper reaction monitoring", Expert Review of Proteomics, Dec. 9, 2013, pp. 551-566, vol. 10, No. 6.
John D. Chapman, et al., "Multiplexed and Data-independent Tandem Mass Spectrometry for Global Proteome Profiling", Mass Spectrometry Reviews, Nov. 26, 2013, pp. 452-470, vol. 33, No. 6.
Christian J. Koehler, et al., "Chapter 10: A Rapid Approach for Isobaric Peptide Termini Labeling", Quantitative Methods in Proteomics, Jan. 1, 2012, pp. 129-141, vol. 893.
Hanno Steen, et al., "The ABC's (And XYZ's) of Peptide Sequencing", Nature Reviews, Molecular Cell Biology, Sep. 2004, pp. 699-711, vol. 5.
International Search Report for PCT/EP2017/070823 dated Oct. 20, 2017 [PCT/ISA/210].
Written Opinion for PCT/EP2017/070823 dated Oct. 20, 2017 [PCT/ISA/237].

\* cited by examiner

LABELLED COMPOUNDS AND METHODS FOR MASS SPECTROMETRY-BASED QUANTIFICATION

CROSS REFERENCE TO RELATED APPLICATIONS

This application is a National Stage of International Application No. PCT/EP2017/070823 filed Aug. 17, 2017, claiming priority based on European Patent Application No. 16185189.4 filed Aug. 22, 2016.

TECHNICAL FIELD

The present invention relates to methods for polypeptide quantification by mass spectrometry wherein combined fragment spectra are acquired. Further, it relates to the use of isotopically labeled peptides in such methods and to methods for their selection.

PRIOR ART

No admission is made that any reference constitutes prior art. The discussion of the references states what their authors assert, and applicants reserve the right to challenge the accuracy and pertinence of the cited documents. It will be clearly understood that, although a number of prior art publications are referred to herein, this reference does not constitute an admission that any of these documents forms part of the common general knowledge in the art.

Proteins provide the framework of life. Therefore, protein identification and quantification are essential tools to approach many biological problems. While single proteins have been analyzed for many years, and the corresponding methods are well established, the field of proteomics emerged only over the past decades. This discipline is concerned with studying not only a handful of proteins at a time, but also complete cellular or subcellular proteomes. Over recent years mass spectrometry, especially ESI-LC-MS (electrospray ionization mass spectrometry), has been the main technology used in proteomics and has proven useful for a host of applications ranging from biomarker discovery and validation to analysis of post-translational modifications.

One standard proteomics workflow for protein analysis includes the following steps: A cellular sample is treated mechanically and with detergents to extract proteins. The extracted proteins are then digested by a protease, most frequently trypsin. The resulting peptide mixture is separated via reversed-phase liquid chromatography (LC) and ionized by electrospray ionization (ESI). The dispersed, charged peptide molecules, so-called precursors, enter the mass spectrometer where each precursor is separately fragmented into shorter amino acid fragments (Steen, H. & Mann, M., 2004. The ABC's (and XYZ's) of peptide sequencing. Nature reviews. *Molecular cell biology*, 5(9), pp.699-711). Finally, the mass-to-charge (m/z) ratios of the fragments of a single precursor are detected and stored in a fragment ion spectrum. Based on the fragment ion spectra the detected peptides and ultimately also the proteins contained in the sample can be identified. Quantification of peptide levels can be done either on the precursor or on the fragment level, depending on the MS method that is used.

Two of the most frequently used mass spectrometry approaches are data-dependent acquisition (DDA), also called "shotgun", and targeted acquisition, such as Selected Reaction Monitoring (SRM). Although both approaches can be used for a wide range of applications, they nonetheless have some drawbacks.

The limitation of DDA is that only a limited number of co-eluting precursors (normally the 5 to 50 most intense) is sequenced during each MS cycle while all other peptides remain unidentified. This leads to an under-sampling of medium- to low-intensity peptides and to missing peptide ID data points as different peptides may be sequenced even in replicate runs of the same sample. Besides, sensitivity is lower compared to targeted mass spectrometry methods. Moreover, DDA has a narrow dynamic range which hampers its suitability for some quantitative studies.

The targeted SRM technique, on the other hand, has a large dynamic range and a high sensitivity. However, SRM requires prior knowledge of target proteins and the number of peptides that can be identified per run is limited, thus making the method unsuitable for discovery studies. Further drawbacks include labor-intense optimization of peptide assays and instrument parameters to detect the target peptides. Additionally, the low resolution and mass accuracy of the quadrupole mass analyzers routinely used in SRM experiments can lead to detection of false-positive signals.

Within the last years, a set of novel MS techniques emerged which improve on the disadvantages of DDA and SRM: These methods are summarized under the term "data-independent acquisition" (DIA) and include techniques such as HRM, SWATH, $MS^E$ and All-Ion-Fragmentation (Chapman, J. D., Goodlett, D. R. & Masselon, C. D., Multiplexed and data-independent tandem mass spectrometry for global proteome profiling. Mass spectrometry reviews, 33(6), pp.452-70; Law, K. P. & Lim, Y. P., 2013. Recent advances in mass spectrometry: data independent analysis and hyper reaction monitoring. Expert review of proteomics, 10(6), pp.551-66). The common feature of most DIA methods is that instead of selecting and sequencing a single precursor peak, larger mass windows, or swaths, are fragmented resulting in complex spectra containing fragment ions of several precursors. This avoids the missing peptide ID data points typical for shotgun methods and potentially allows sequencing whole proteomes within one run, which offers a clear advantage over the small number of peptides that can be monitored per run by SRM. Furthermore, DIA techniques such as SWATH have excellent sensitivity and a large dynamic range. To identify the peptides present in a sample, the fragment ion spectra can be searched against theoretical spectra or can be mined using SRM-like transitions. The detected fragments are subsequently arranged in SRM-like peak groups.

In addition to the DIA methods mentioned above, a novel targeted proteomics technique was developed which can be considered a successor of SRM. This method, called parallel reaction monitoring (PRM), relies on a quadrupole mass filter which is combined with a high resolution mass analyzer, such as e.g. in a quadrupole-equipped bench-top orbitrap MS instrument. Replacing the last quadrupole of a triple quadrupole with a high resolution mass analyzer allows the parallel detection of all fragment ions at once. In principle it would also be possible to combine a linear ion trap with the orbitrap instead of the quadrupole. The advantage of PRM over SRM is that less prior knowledge about the target molecules is required. In terms of dynamic range PRM performs even better than SRM under some conditions due to its high selectivity.

A further development of this technique is multiplexed parallel reaction monitoring (mPRM) wherein not only single precursors are fragmented. In this method fragment ion spectra containing fragment ions from several precursors are created by either fragmenting larger m/z ranges or by multiplexing, which is sequentially fragmenting several precursors, and storing their fragment ions together for later measurement. In a further development internal standard triggered-parallel reaction monitoring (IS-PRM) has been proposed. In this method internal standard peptides are added to the sample. Based on their detection in a fast, low-resolution "watch" mode the acquisition parameters are switched to "quantitation" mode to ensure acquisition of endogenous peptides. This dynamic data acquisition minimizes the number of uninformative scans and can be applied to a variety of biological samples.

In proteomics experiments peptide levels in a sample are often determined relative to a labeled standard. Especially, isotopic labeling in combination with DDA and SRM mass spectrometry has proven useful to address a wide range of biological questions. In one exemplary setup, a sample containing endogenous, unlabeled, "light" peptides in unknown amounts is mixed with known quantities of synthetic, isotopically labeled, "heavy" peptides. During mass spectrometry analysis of the mixture, the mass difference introduced by the isotopic labels allows to distinguish the light endogenous from the heavy synthetic peptides in the sample and allows for their separate quantification.

Such experiments have proven so successful that pools of heavy-labeled synthetic peptides are now readily available from several commercial vendors. Alternatively, heavy-labeled peptide pools can also be produced via metabolically labeling proteins with heavy amino acids, or directly with heavy elemental isotopes, during in vitro or in vivo expression, and digesting said protein to peptides. The advantage of synthesizing peptides is that it is much faster and purification as well as absolute quantification of synthesized peptides is easier. Furthermore, incorporating only one heavy-labeled amino acid, rather than heavy elemental isotopes such as $^{15}N$ for the whole peptide, has the advantage of producing a constant mass shift.

US2014248603 provides methods and mass-labeled peptides for use in said methods for quantifying the presence of a one or more viral proteins in a sample of a preparation containing agents which bind to said viral protein, using mass-spectroscopic analyses of the sample and standards containing known amounts of labeled and unlabeled signature peptides, in particular wherein said viral proteins are antigens in a vaccine for porcine circovirus.

SUMMARY OF THE INVENTION

In proteomics often the protein levels in an endogenous sample and in a reference standard need to be compared. To achieve this, the sample (containing unlabeled proteins and/or peptides) and the reference standard (containing labeled proteins and/or peptides) are combined and the mixture is measured by mass spectrometry.

Usually, the reference peptides are labeled at their C-terminus with a single amino acid containing heavy elemental isotopes. Preferably, the labeled amino acids are arginine or lysine containing at least one, usually 6-10 atoms of $^{13}C$ and/or $^{15}N$. When these labelled reference peptides are fragmented during MS analysis, all C-terminal fragment ions, such as y-ions, x-ions, and z-ions will contain the heavy labeled amino acid and will have masses that are distinct from their unlabeled counterparts. However, N-terminal fragment ions, such as b-ions, a-ions, and c-ions will not contain the C-terminal amino acid label. Thus, they have masses identical to the masses of the corresponding N-terminal ions, e.g. b-ions, resulting from unlabeled peptides. We call this "fragment overlap". Obviously, fragment overlap might not only occur between labeled and unlabeled peptides but also between two variants of peptides differing in a single label, i.e. in the label's properties and/or in its position.

Throughout the application we will use b-ions to discuss N-terminal fragment ions and y-ions to discuss C-terminal fragment ions. However, the described effects are not limited to b- and y-ions, but equally apply to the other N-terminal fragment ions (e.g. a-, c-ions), and/or C-terminal fragment ions (e.g. x-, z-ions), respectively.

Fragment overlap does not affect the experiment if the mixture of labeled and unlabeled peptide variants is analyzed by DDA or SRM since both methods only fragment one precursor at a time and collect fragment ions of different precursors in different spectra. The mass difference introduced is typically large enough that the two precursors can be separately selected by the mass spectrometer. However, it becomes an issue whenever mass spectrometry methods are used wherein the fragment data for the two variants of each peptide are combined, e.g. whenever a combined fragment ion spectrum of the labeled and the unlabeled peptide variants together is acquired and/or stored. This is the case for all DIA MS methods as well as mPRM. Since the stored fragment ion spectra contain fragments from heavy and light precursors, and since N-terminal fragment ions cannot be assigned to either peptide variant based on their mass alone, the N-terminal fragment ions (such as b-ions) cannot be used for quantification. This is a problem that occurs not only for a handful of peptides, but for all labeled peptides in such experiments. Thus, for all peptides in a sample, all N-terminal fragments are eliminated for data analysis. To further aggravate the problem, the presence of shared fragments between two peptide variants further complicates data analysis and hampers peptide identification for instance when the known relative fragment ion intensity is used for scoring.

Thus, DIA and multiplexed PRM quantification methods relying on isotopic labeling have not yet reached their full potential and could be further improved. A modified approach is desired to reconcile the DIA and mPRM technologies with isotopic labeling and to reduce fragment overlap. Despite the many technological advances in the proteomics field in recent years, a solution has not yet been proposed for this problem.

The present invention was made in view of these problems and of the prior art described above. The object of the present invention is to provide a way to reduce fragment overlap between fragments of unlabeled and labeled peptides in quantification experiments wherein data entities contain combined fragment data from both variants. Especially, the present invention relates to reducing the fragment overlap between N-terminal fragment ions of isotopically unlabeled and labeled peptides.

The way to achieve this is by selectively introducing a second label into the labeled peptides, such that the majority of the fragments of interest resulting from the unlabeled and the labeled variants differ in a label i.e. in the labels' properties and/or position. For example one can selectively introduce an isotopically labeled amino acid towards the N-terminus of synthetic peptides in addition to a label located towards the C-terminus.

The difference in multiple labels results in distinct fragment series for unlabeled and labeled peptides. Thus, the fragments stemming from the different peptide variants will be distinguishable even if they are combined in one data storage unit, e.g. when they are acquired together, or are acquired separately and then combined. The absence of fragment overlap not only allows the separate quantification of the fragments from unlabeled and the labeled peptides. It also facilitates data analysis and increases the number of fragments that can be used for quantification compared to mixtures where the unlabeled and the labeled peptides differ only in a single, terminal label.

Generally speaking, the present invention therefore proposes a method for the absolute or relative quantitative analysis of proteins and/or peptides with or without post translational modification(s) using a mass spectrometry method. In this method in a first step unlabeled proteins from an endogenous mixture are digested and subsequently digestion products thereof selected, in a second step said digestion products are fragmented, and in a third step a combined fragment spectrum is acquired comprising b-ions as well as y-ions of said digestion products.

According to the proposed method, at least one reference peptide with or without post translational modification(s) is added to said mixture before and/or after digestion in either
   a known concentration in case of absolute quantification or
   in always the same concentration in a series of experiments for relative quantitative analysis.

Said at least one reference peptide is selectively isotopically labeled by having incorporated
   one isotopically labeled amino acid forming its very C-terminus or being one of the four terminal amino acids at the C-terminus and additionally
   one further isotopically labeled amino acid forming its very N-terminus, or being one of the four terminal amino acids at the N-terminus.

The "isotopically labeled amino acid forming" the respective terminus is to be understood that the atoms of the respective amino acid are isotopically labeled (irrespective of any possible additional chemical modification of the respective amino acid). The labelling is thus present in the atoms of the respective amino acid and not in e.g. any chemically modifying moiety such as a post translational modification structural element of the peptide.

The labelled reference peptide may be free from any post translational modification, i.e. built exclusively from any unmodified naturally occurring proteinogenic amino acids (the 21 amino acids that are directly encoded for protein synthesis by the genetic code of eukaryotes).

The labelled reference peptide may however also be post translationally modified. The labelling in this case is still given by the actual isotopically labeled amino acids forming the respective terminus and not by a labelling of the post translational modification structural elements.

The said at least one reference peptide, which is added to said mixture in a known concentration in case of absolute quantification or in always the same concentration in a series of experiments for relative quantitative analysis, is fragmented, acquired, and stored in said combined fragment spectrum comprising also b-ions and y-ions of said digestion products, preferably of the endogenous peptide corresponding to the labeled reference, Within the present application a (reference) peptide comprises or consists of 5-100, preferably 7-30, most preferably 10-20 amino acids.

The solution of introducing multiple labels has not been considered in the past inter alia since labels are challenging to provide and thus expensive, and the costs and time investments for introducing multiple labels are normally high. This is especially true for the complex synthesis of quantified heavy-labeled peptides. Even synthesizing a pool of single-labeled peptides is typically at a level of complexity, which lies outside the time and resources that most research groups have available for one experiment. This is emphasized by the fact that many quantification experiments can still be completed despite the occurrence of fragment overlap although they do not reach their full potential. For example DIA experiments using single-labeled peptides can be executed by relying only on y-ions for quantification and without using the b-ions for all peptides for quantification. However, a big part of the available fragment information will remain unused. The covert need for improvement in combination with the high label costs lead the skilled person away from the solution provided by the present invention.

As opposed to its usefulness for DIA and mPRM studies, multiple-labeling of peptides does not add any benefit for most proteomics applications and therefore has not been adopted in the field. WO2002083923 mentions on a side note that peptides can carry more than one label in connection with de-novo peptide-sequencing, but fails to relate to the fragment overlap problem occurring in DIA or mPRM experiments, and fails to address where the labels shall be placed to solve the problem occurring in DIA or mPRM experiments.

The set of labeled peptides of the current invention can be used for relative quantification of unlabeled peptides in a sample relative to the amount of their labeled variants of the present invention. Furthermore, if the amount of the labeled peptides in the set of the current invention is known, the set can be used for absolute quantification of their unlabeled variant.

To distinguish N- and C-terminal fragment ions from labeled and unlabeled peptides, the labeled peptides can contain two labels at two different positions in the peptide. In one embodiment, the unlabeled peptides differ from their labeled peptide variants in two labels, i.e. in the labels' properties and/or in their position, wherein the labels were introduced selectively. Preferably, the labeled peptide contains two labels not present at the same position in the unlabeled peptide variant. In either case, the labels can be located at the termini of a peptide, or at any other position.

Preferably in said reference peptide, apart from the one single isotopically labeled amino acid at or close to the C-terminus and the one single isotopically labeled amino acid at or close to the N-terminus, not more than one additional amino acid is isotopically labeled, preferably no additional amino acid is isotopically labeled, so there is only one label at or close to the C-terminus, and one additional label at or close to the N-terminus.

Close to the C-terminus, and close to the N-terminus in this application is to be understood as follows: close to the C-terminus means the isotopically labeled amino acid is one of the four terminal amino acids at the C-terminus, preferably it is one of the three or two most terminal amino acids at the C-terminus. Close to the N-terminus means the further isotopically labeled amino acid is one of the four terminal amino acids at the N-terminus preferably it is one of the three or two most terminal amino acids at the N-terminus.

Preferably, in said reference peptide one (preferably single) isotopically labeled amino acid is forming its very C-terminus and one further (preferably single) isotopically labeled amino acid is forming its very N-terminus.

Preferably the one isotopically labeled amino acid is one of the three or two most terminal amino acids at the C-terminus and additionally the one further isotopically labeled amino acid is one of the three or two most terminal amino acids at the N-terminus.

Said post translational modification can be one or more selected from phosphorylation, acetylation, methylation, sulfation, hydroxylation, lipidation, ubiquitylation, sumoylation, glycosylation, oxidation, and carbamidomethylation.

Various mass spectrometry setups suitable for the analysis of proteins and/or peptides can be used for the quantitative analysis in the present invention. In a preferred embodiment the mass spectrometry setup is liquid chromatography MS (LC-MS).

Various ionization techniques suitable for the ionization of proteins and/or peptides can be coupled to the MS setup, e.g. matrix-assisted laser desorption/ionization (MALDI) or electrospray ionization (ESI).

Various fragmentation techniques suitable for fragmenting proteins and/or peptides can be employed during experiments with the current invention. Examples include collision-induced dissociation (CID), electron-capture dissociation (ECD), electron-transfer dissociation (ETD), negative electron-transfer dissociation (NETD), Pulsed Q Collision Induced Dissociation (PQD), and Higher-energy C-trap dissociation (HCD). Moreover, fragmentation levels can be MS2, MS3, MSn.

The invention is especially useful for peptide quantification studies by DIA or mPRM methods. However, various mass spectrometry methods can be employed where combined fragment ion spectra containing fragment data of both labeled peptides and unlabeled peptide variants are stored. This includes but is not limited to data-independent acquisition (DIA) methods. The literature describes numerous DIA methods and new ones are continuously becoming known. Methods which can be used in the present invention include but are not limited to HRM, SWATH, $MS_E$, PAcIFIC, and All-Ion-Fragmentation. Moreover, also multiplexed parallel reaction monitoring (mPRM) can be used as mass spectrometry acquisition method.

The use of a specific mass spectrometry instrument is not critical for the present invention. For example, a mass spectrometer capable of performing DIA with a sufficient resolution can be employed such as a Quadrupole-Orbitrap, Quadrupole-TOF, IMS-TOF, Quadrupole-IMS-TOF, IMS-Quadrupole-TOF, IMS-Orbitrap, Quadrupole-IMS-Orbitrap or IMS-Quadrupole-Orbitrap instrument. Furthermore, a mass spectrometer capable of performing multiplexed PRM can be employed as long as it has a means to select precursor ions for fragmentation and store fragment ions before measuring the multiplexed spectrum. Examples are Quadrupole-Orbitrap, IMS-Orbitrap, Quadrupole-IMS-Orbitrap, IMS-Quadrupole-Orbitrap instrument or Linear Ion Trap-Orbitrap instruments. Moreover, also another mass spectrometer or device capable of fragment-based analysis can be used if combined fragment ion spectra containing fragment data of both labeled peptide of the present invention and their unlabeled peptide variant are produced from its data during acquisition.

Using labeled peptides which differ in at least two labels from the unlabeled variant they are compared with, reduces fragment overlap. This has the advantage that more fragments are available for quantification, e.g. N-terminal fragment ions, such as b-ions. Since b-ions make an important contribution to the total ion intensity in HCD peptide spectra and to the amino acid coverage, especially for longer peptides, the quantification is more robust. Furthermore, the increased number of available ions makes more peak groups amenable to quantification and the fragment ion spectra contain less shared ions between heavy and light peptide variants. This contributes to an increase in the number and quality of peptide identifications. Moreover, it remains to note that such labeled peptides which differ in at least two labels from the unlabeled variant they are compared with, as provided by the present invention, are also suitable for applications for which traditionally labeled peptides which differ in only a single label are used.

Preferably said combined fragment spectrum is acquired using a full-range mass isolation window, or a mass isolation window having a width in the range of 2-1000 Thomson or 5-100 Thomson, preferably of 5-30 Thomson, most preferably of 10-25 Thomson. Typically, but not necessarily, wide mass isolation windows (for example >100 Thomson) are used if other or additional means of separation apart from liquid chromatography are used, such as IMS. The Thomson unit is common in the field of mass spectrometry as a unit of mass-to-charge ratio, $1Th=1u/1e=1.036426\times10^{-8}$ kg $C^{-1}$.

The present invention further proposes a method for selecting the label and label position of at least one suitable reference peptide for use in a method as described above, wherein the position of the label at the C-terminus, or within the four terminal amino acids at the C-terminus, and/or the position of the label at the N-terminus, or within the four terminal amino acids at the N-terminus, is selected in a way that the majority of the relevant fragment ions from a selectively double-labeled peptide differ from the corresponding fragment ions from the unlabeled peptide, preferably using a procedure which, inter alia, takes into account of at least one of the following parameters or a combination thereof: the availability and/or cost of the labeled version of the corresponding amino acid at the respective position; the complexity of the incorporation of the labeled version of the corresponding amino acid at the respective position, the occurrence of the corresponding amino acid in the corresponding reference peptide and positions thereof, wherein the label is preferably selected so as to be optimized with respect to these parameters.

One crucial factor for the present invention is the positioning of the labels within each selectively labeled peptide. Ideally, the labels are placed in a way that the majority of the relevant fragment ions from a selectively double-labeled peptide differ from the corresponding fragment ions from the unlabeled peptide by at least one label, i.e. in the spectrum by the mass difference between the respective labeled amino acid and the corresponding unlabeled amino acid at the respective (terminal) position.

Following the peptide fragmentation pattern a first label must be located at or close to the C-terminus and a second label at or close to the N-terminus of each peptide in order for all N- and C-terminal fragments to carry a label.

The availability of a label and/or the complexity of its incorporation is reflected in the synthesis cost. Labeling the N- and C-terminal amino acids in many cases may and will not be the simplest and as a consequence not the most economic choice. Other amino acids more distant from the termini may be easier to obtain or incorporate and therefore priced at a lower rate. Therefore, also financial aspects need to be taken into consideration when choosing labels and label positions. Additionally, the very small terminal ions (e.g. b1, b2, y1, y2) of each ion series convey only little information and oftentimes it is not essential to detect these fragment ions. Therefore, it makes sense to balance the necessity of having also these terminal fragment ions labeled with other considerations, such as facility of obtaining and incorporating an amino acid. With price being a good indicator for the accessibility of an amino acid, one way to do this is to select the amino acid with the lowest label cost within a stretch of amino acids from the termini wherein the length of the stretch is selected such that most of the fragment ion information content is retained. Using such a procedure, the total label costs for synthesizing a set of several thousand peptides can be reduced substantially with only a small loss of information.

Labels can be expensive and the costs and time investments, as well as the technical resources, for introducing one or more labels into one or more peptides can be high. Furthermore, not all types of labels may be readily available or suitable for a certain proteomics application. Therefore, a prior analysis of the set of peptides helps to select optimal labels or label positions, to estimate the expected total label costs, and to optimize the experimental setup in order to minimize said costs. Furthermore, other factors have to be taken into account, such as the information content provided by different label positions, and the availability of the different labels. However, the large numbers of peptides analyzed in proteomics studies complicate any prior analysis of the set of peptides. Therefore, a method which is capable to do any or several of the following among other operations offers a considerable advantage: to estimate total label costs, to select the optimal labels and/or label positions, and/or to determine the most cost-efficient way of labeling the peptides. Furthermore, in the course of such an analysis one may also determine other parameters which are helpful for planning experiments using multiply-labeled peptides, e.g. they might simulate fragment collisions.

The present invention further proposes a reference peptide or set of reference peptides for use in a method as described above and/or determined as described above, wherein said reference peptide, and/or at least one or a plurality or all of the reference peptides in the set of reference peptides, is selectively isotopically labeled by having incorporated one (single) isotopically labeled amino acid forming its very C-terminus or being one of the four terminal amino acids at the C-terminus and one (single) further isotopically labeled amino acid forming its very N-terminus, or being one of the four terminal amino acids at the N-terminus.

The post translational modification(s) can be any modification occurring on peptides and/or proteins. Preferably it is selected from phosphorylation, acetylation, methylation, sulfation, hydroxylation, lipidation, ubiquitylation, sumoylation, glycosylation, oxidation, and carbamidomethylation.

The present invention can be used to analyze peptide mixtures of a wide range of complexities. This includes the analysis of single proteins and/or peptides, as well as for large numbers thereof. However, the present invention is particularly suited for the analysis of whole or partial proteomes and of mixtures comprising peptides from 100 or more proteins or comprising at least 100 peptides.

The set of labeled peptides of the present invention and its methods comprises a number of peptides of interest. The peptide sequences in said set can for example be selected from a peptide spectral library. This peptide spectral library can e.g. result from a previous acquisition of a sample of the same cell type or organism or even of the same sample.

The set of labeled peptides of the present invention can be obtained with an appropriate method capable of introducing labels at the desired positions. One preferred way is to synthesize the labeled peptides. During synthesis labels, such as amino acids containing heavy elemental isotopes, can be readily incorporated. An advantage of synthesizing peptides is its speed and that the synthetic peptides can be easily purified and their amounts quantified. Another route for obtaining sets of labeled peptides is by in vitro translation of peptides in the presence of labels. Yet another route for obtaining labeled peptides is by in vitro translation of proteins, followed by an enzymatic or chemical digestion if necessary. Yet another route for obtaining labeled peptides is by in vitro translation of proteins, adding them to the unlabeled proteins, followed by an enzymatic digestion together with the sample. Yet another route is to enzymatically or chemically cleave proteins or polypeptides in the presence of labels, e.g. in $^{18}O$-containing water, in a way that labels are incorporated at the cleavage site. Yet another route to introduce a label during the production of the labeled peptides of the present invention is by enzymatic reaction. For example, N-terminal arginylation by the yeast arginyl-tRNA protein transferase (ATE) enzyme has been described. This enzyme recognizes acidic amino acids or oxidized cysteine residues at N-termini of peptides and adds an N-terminal arginine residue. Any similar enzymatic reaction that adds terminal labels could in theory be used for introducing labels which potentially results in suitable labeled peptides. It remains to note that some of the above-mentioned methods could potentially produce peptides which do not have any isotope envelope but only show a limited number or even only a single isotopic peak, e.g. by adding only monoisotopic versions of amino acids during peptide synthesis.

The set of labeled reference peptides/proteins of the present invention can be comprised in an appropriate kit wherein the composition of the elements of the kit can be chosen as needed. They are especially suited to be contained in a kit in lyophilized form. The kit may comprise further components including but not limited to, buffers to dissolve and/or dilute the compounds.

The present invention can be used for analyzing a variety of peptides and/or proteins from a variety of sources. The peptides and/or proteins can be extracted from samples selected from but not limited to whole organisms, tissues, cells, body fluids, and compound mixtures. For example, the present invention can be used in peptide abundance measurements in samples from a variety of organisms, tissues, bodily fluids, and peptide mixtures. The present invention is especially suitable for any sample amenable to proteomics applications. For such proteomics applications the only requirements for the sample are that peptides can be obtained from the sample, that a peptide spectral library, either theoretical or experimental, covering the expected peptide content is available or can be created, and that the desired multiply-labeled peptides can be produced. The present invention is particularly suited for the analysis of organisms, cells, and tissues types whose proteomes have been fully or partially annotated. These include but are not limited to whole organisms, parts, tissues, or cells of *Homo sapiens, Mus musculus, Arabidopsis thaliana, Saccharomyces cerevisiae, Escherichia coli, Caenorhabditis elegans, Bacillus subtilis* and *Drososphila melanogaster*, rat, tobacco, and maize.

The present invention is especially suited for the analysis of human blood, as well as human blood plasma, human blood serum, human urine and human CSF.

The present invention provides a solution to the above mentioned problems. Furthermore, it takes into account the latest technological developments in proteomics, which made the previously unaddressed fragment overlap problem especially and unexpectedly relevant for this field.

Definitions:

Amino acid: embraces naturally occurring amino acids, as well as non-natural amino acids, amino acid analogs, and amino acid derivatives. These can also be proteinogenic amino acids carrying PTMs.

Combined fragment spectrum: defines a mass spectrometry spectrum which was acquired using DIA or mPRM or another suitable mass spectrometry method and which contains fragment ions from multiple precursors.

Data-independent acquisition or DIA: defines mass spectrometry methods where the stored fragment ion spectra contain fragment ions from multiple precursors. The term includes but is not limited to methods such as HRM, SWATH, all-ion-fragmentation, $MS^E$, PAcIFIC, or any other method not mentioned here by name but employing similar principles as the aforementioned methods. Fragment collisions: defines the phenomenon that some non-corresponding fragment ions of differently labeled peptide variants have the same masses. For example a fragment collision occurs if b5 from a heavy-labeled peptide has the same mass as y4 of a light peptide.

Fragment overlap: defines the phenomenon that corresponding fragment ions of differently labeled peptide variants, e.g. light and heavy-labeled variants, have identical masses due to the absence of any differing label in said fragments. For example a fragment overlap occurs if y5 from a heavy-labeled peptide has the same mass as y5 of a corresponding light peptide, or if b5-ions of both, light and heavy peptide variants, have the same mass.

Human blood: refers to whole blood, blood plasma, blood serum, derivatives or a subfraction of any of the preceding.

Ion mobility separation, or IMS: refers to an analytical technique used to separate ionized molecules in the gas phase. IMS can be combined with mass spectrometry analysis (IMS-MS). It is assumed that normally unlabeled and labeled peptides have identical or very similar drift times.

Label: defines an artificial isotopic label that can be introduced into a protein and/or peptide, thereby increasing the mass of the protein and/or peptide and/or of a corresponding fragment. Labels can be selected from isotopically labeled amino acids containing heavy or light elemental isotopes. In the labeled peptide, the isotopically labeled amino acid replaces the corresponding unlabeled amino acid which is present at the same position in the unlabeled peptide variant.

Isotopically labeled amino acid: is an amino acid in which at least one atom, preferably all atoms of one kind, is replaced by a different, stable, naturally not occurring or rarely occurring isotope. In a preferred embodiment, the isotopes are derived from any of the following elements: C, H, N, O, S. In a more preferred embodiment, the isotopes are one or more of $^{13}C$, $^2H$, $^{18}O$, $^{15}N$, $^{32}S$. Preferably the isotopically labeled amino acid is at least partly or fully labeled in $^{13}C$, $^{15}N$, and/or deuterium.

Label cost: defines the price of a label, e.g. the price per mmol or mg or microliter of a heavy elemental isotope containing amino acid.

Multiplexed PRM or mPRM: defines a mass spectrometry method wherein PRM is multiplexed such that the fragment ions of several target proteins and/or peptides are stored together. In this method fragment ion spectra containing fragment ions from several precursors are created by either fragmenting larger m/z ranges or by multiplexing, which is sequentially fragmenting several precursors, and storing their fragment ions together for later measurement.

Multiply-labeled: refers to a variant of a peptide containing three or two selectively placed labels.

Peptide spectral library: defines an electronic assembly comprising at least one peptide spectrum, or a list comprising at least one peptide sequence and/or spectral data. A spectral library can be obtained either theoretically, e.g. based on expected fragment masses for known peptide sequences, or experimentally, e.g. based on peptide identifications in measurements.

PRM or parallel reaction monitoring: defines a targeted mass spectrometry method wherein precursor ions are isolated and are fragmented. This is followed by detection of all fragment ions in a high resolution mass analyzer for example an Orbitrap or TOF. For quantification in PRM one or more fragment ions are extracted as "pseudo-transitions" that are selected post-acquisition.

Total label cost: defines the summed up price for all labels used to label a certain amount (e.g. in mmol, mg, ml) of a specific set of proteins and/or peptides with a specific value of $n_{globalMaxVal}$. This only includes the costs for the labels but no other costs, such as e.g. the costs for unlabeled amino acids or further synthesis costs.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Herein after, the present invention is described in further detail and is exemplified. However, the examples are not intended to limit the present invention. Unless defined otherwise, all technical and scientific terms used herein have the same meaning as commonly understood by one of ordinary skill in the art to which this invention belongs. It must be noted that as used herein and in the claims, the singular forms "a", "an", and "the" include plural referents unless the context clearly dictates otherwise. Thus, for example reference to "a label" includes a plurality of such labels and so forth.

Although any materials and methods similar or equivalent to those described herein can be used to practice or test the present invention, the preferred materials and methods are now described.

This description specifically details the application of labeled reference peptides in quantitative proteomics studies wherein combined fragment ion spectra are obtained. It describes methods for the quantitative analysis of peptides and/or proteins, methods for the selection of suitable reference peptides and label positions, and the reference peptides used in said methods. Different aspects relating to the experimental setup, and labeling strategies are discussed. Finally, examples of applications illustrate the potential of the methods and substances of the present invention to improve the accuracy of quantitative studies.

Mass Spectrometry Methods:

Mass spectrometry (MS) methods are widely used for peptide and/or protein identification and quantification, especially in proteomics studies where large numbers of analytes are monitored. A standard sample preparation workflow for bottom-up liquid chromatography (LC)-MS experiments includes the following steps: Proteins comprised in a sample are digested to peptides using a protease such as trypsin. The peptides are then separated by liquid chromatography, most commonly via reversed-phase liquid chromatography (LC). As soon as the peptides elute from the chromatography column, they are ionized by electrospray ionization (ESI): At the ion source, a voltage is applied which disperses the liquid sample into fine droplets containing charged peptide molecules. These precursors then enter the mass spectrometer where they fly in an electric field and are resolved according to their mass-to-charge (m/z) ratio. Finally, the precursor ions are detected and their mass-to-charge (m/z) ratio is registered, resulting in MS1 (or MS) spectra acquired over the whole gradient. Single peptide precursors or wider mass ranges are sequenced as follows: The ions in the selected mass window are isolated and fragmented, e.g. by collision with Helium gas, a process termed collision-induced dissociation (CID) or by higher energy C-trap dissociation (HCD). All fragment ions are then recorded in one MS/MS, MS2, or fragment ion spectrum.

Figure 2:
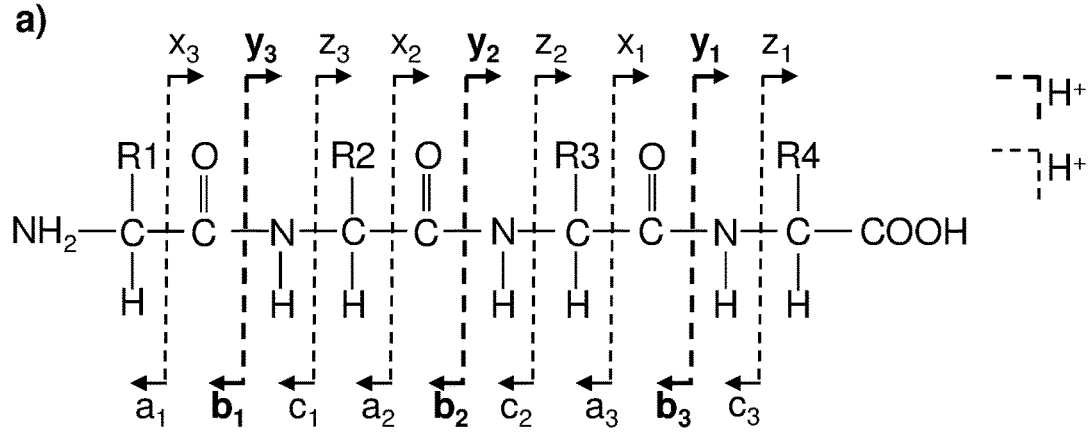
FIG. 2 shows schematic drawings of a) a peptide fragmentation pattern and b) of a peptide and its y- and b-fragment ions.
Figure 2:
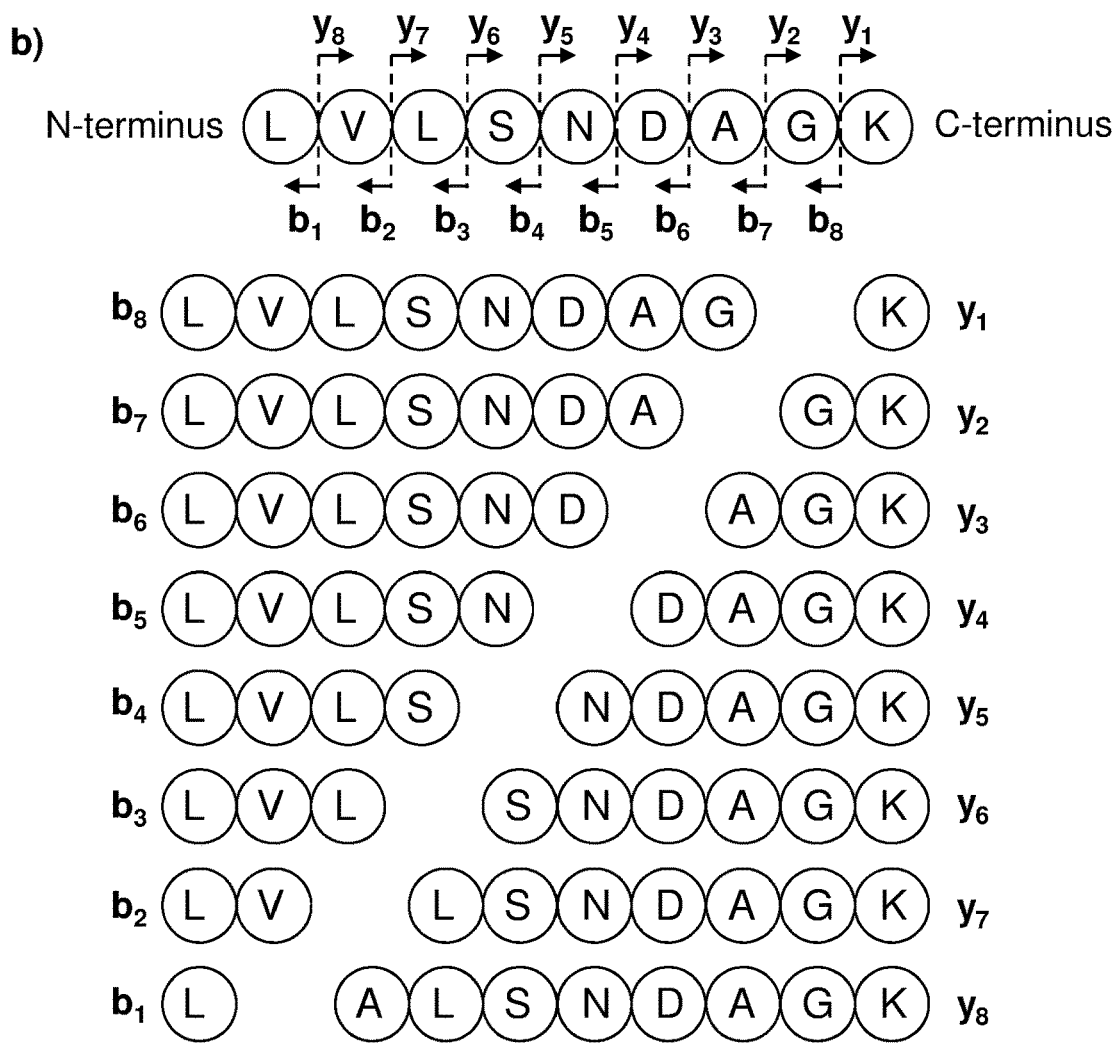

The fragment ion spectra serve as a basis for peptide identification. Peptides do not disintegrate randomly during fragmentation, but rather fragment according to a pattern into a, b, c, x, y, and z-ions (FIG. 2a). In common proteomics studies, the most prominent ion series are often y- and b-ions and special attention is paid to them. These two form complementary fragment ion series (FIG. 2b), wherein y-ions include the peptide's C-terminus and b-ions include the N-terminus. Since peptide fragmentation follows a known pattern, the peptide sequence can be derived from the fragment ion peaks in an MS2 spectrum. Once the peptide has been identified, it can further be quantified using the acquired MS1 or MS2 data.

Different mass spectrometry approaches can be used in bottom-up proteomics experiments. While the basic steps of the protocols remain the same for all approaches, other parts, such as fragmentation, identification, and quantification of peptides, vary depending on the MS method used.

Figure 3:
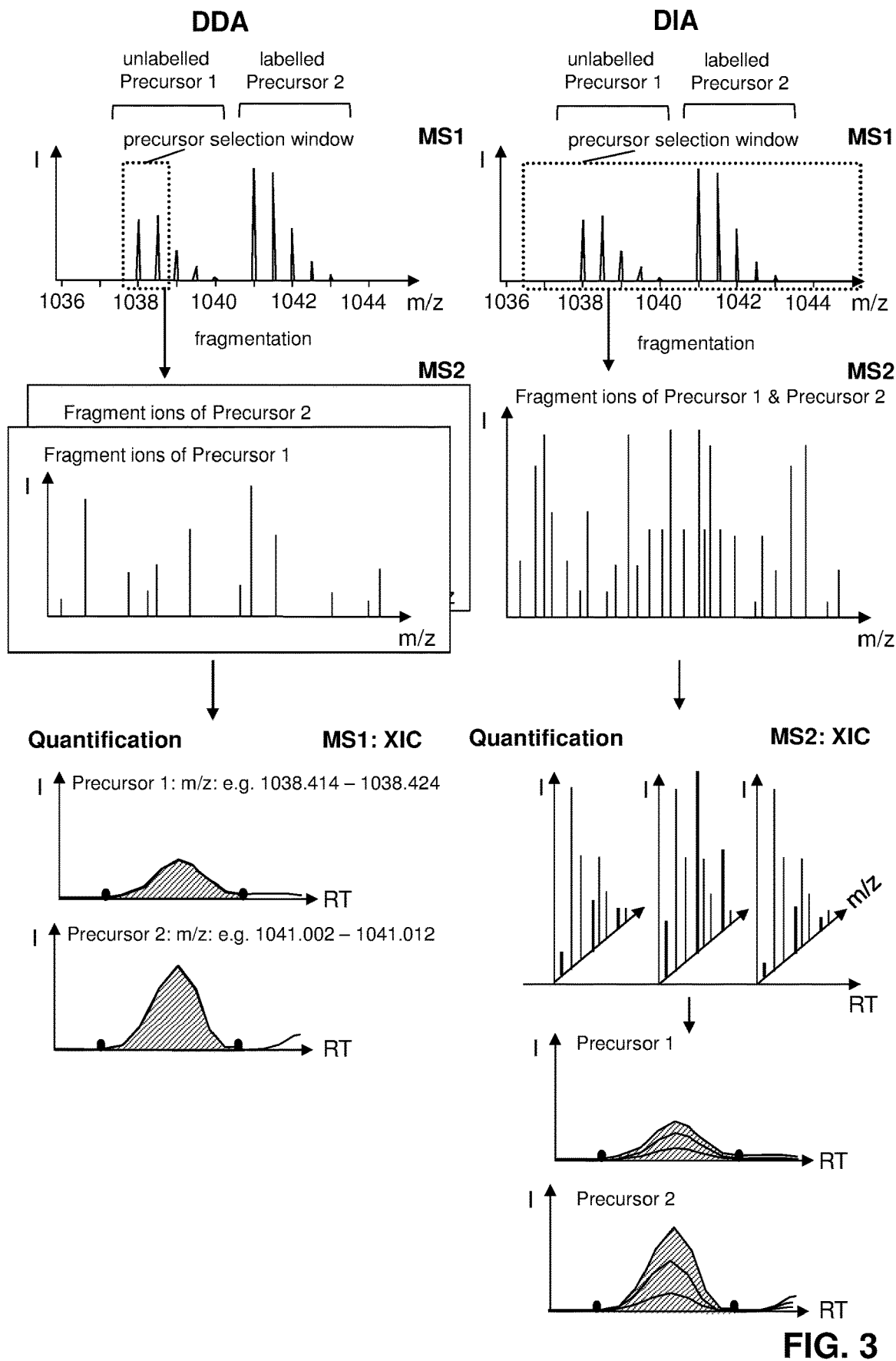
FIG. 3 shows a schematic drawing comparing DDA with DIA, wherein mass windows containing several precursors are fragmented in the data-independent acquisition experiment and the resulting data are stored in combined fragment ion spectra.

One of the most frequently used mass spectrometry approaches in proteomics is data-dependent acquisition (DDA), also called "shotgun" (FIG. 3, left panel). In a classical data-dependent workflow only the precursors with the highest signal intensities in the MS1 spectrum are sequenced: The ions in a small mass window around the desired precursor m/z are isolated and fragmented (FIG. 3, left panel). All fragment ions derived from this small mass window are then recorded in one MS/MS, MS2, or fragment ion spectrum. To identify the peptides and proteins contained in the sample, the MS/MS spectra are searched against a database containing the theoretical spectra of the whole proteome of interest. After the peptides have been identified, peptide and/or protein quantification is typically done on the MS1 level by creating extracted ion chromatograms (XIC), i.e. by monitoring the signal of a certain precursor m/z peak over the LC gradient. Since it can identify thousands of proteins with minimal prior knowledge about a sample's protein content, DDA is widely used for discovery studies. However, a disadvantage of the DDA approach is that only a limited number of precursors is selected for fragmentation. As a consequence many peptides remain unidentified. Furthermore, changes in precursor intensities can result in different sets of peptides being sequenced even in replicate MS acquisitions of the same sample. Additionally, sensitivity is lower compared to other mass spectrometry approaches.

Within the last years, data-independent acquisition (DIA) emerged as a new MS approach which remedies many of DDA's disadvantages. Techniques which are based on this principle include for example HRM, SWATH, $MS^E$ and All-Ion-Fragmentation. The core feature of all DIA methods is that instead of a single precursor as for DDA, larger mass windows, or swaths, containing multiple precursors are fragmented (FIG. 3, right panel). Usually, a quadrupole acts as a mass filter here and targets certain mass ranges for fragmentation. The resulting fragment ions are then acquired on a high resolution mass analyzer, such as a time-of-flight (TOF) or an Orbitrap. This produces complex MS2 spectra (combined fragment ion spectra) containing fragment ions of several precursors. Due to the complexity of the MS2 spectra, it is vital to acquire fragment ions with high resolution and high mass accuracy in order to later assign the different fragments to their corresponding peptide precursors.

Data analysis can be challenging due to the spectra containing fragments of several peptides.

To identify and quantify the peptides present in a sample, the combined fragment ion spectra can be searched against a spectral library, or theoretical spectra or can be mined using SRM-like transitions. Fragments from the same peptide are subsequently arranged in SRM-like peak groups: The signal corresponds to the intensity of each fragment monitored over time in sequential spectra. Fragments of the same peptide will produce similarly shaped elution peaks with maxima at identical retention times (RT). These SRM-like peak groups can then be used to quantify e.g. an unlabeled endogenous peptide versus a labeled reference peptide. I.e. the quantification is done based on MS2 level data. Alternatively, peptide and/or protein quantification can be done on MS1 level if the corresponding MS1 data was acquired.

The same data analysis concepts can be applied to the analysis of DIA and mPRM data. Traditionally, a spectral library generated from DDA-data is employed to extract quantitative features from DIA or mPRM runs and to identify peptides and/or proteins. Alternative data analysis approaches exist which do not rely on DDA-based spectral libraries, or do not rely on them exclusively: For example, mPRM or DIA data containing MS1 and MS2 scans can be converted into MS2 spectra containing fragment ions relevant for a specific MS1 feature. These spectra are searched using a database of theoretical spectra which results in peptide identifications being assigned to the precursor-fragment matches. This process is very similar to how DDA data is typically processed. The search results can be saved as spectral library. Furthermore, a spectral library can be generated from combined search results from DIA and/or DDA experiments, or from mPRM and/or DDA experiments. In either case, the search results and/or the spectral library are used to extract quantitative information from the mPRM or DIA runs, allowing peptide and/or protein quantification on MS1 and/or MS2 level.

In summary, a spectral library can be generated from many sources including but not limited to the following: from data of the same acquisition, from a previous acquisition of the same sample, from an independent acquisition of a similar tissue or complete organism, from published data, from mPRM data, from DIA data, from DDA data, from a combination of DIA and DDA data, from a combination of mPRM and DDA data, from a resource database from fractionated or unfractionated samples, it can be generated on-the-fly from DIA or mPRM data, or from a combination of sources mentioned above. The spectral library can be saved and/or can be discarded after use.

The following paragraph provides non-limiting examples for different data analysis approaches for DIA and/or mPRM data. A spectral library can be generated from the same sample, a similar sample, or from resource data. The data for the spectral library can stem from fractionated and/or unfractionated samples. The data for the spectral library can have been acquired with different mass spectrometry methods such as DDA, targeted mass spectrometry methods, DIA or mPRM, or any combination of them. The sample to be quantified can be fractionated or unfractionated and is acquired by DIA and/or mPRM. Peak groups and peptides in the sample are identified using the spectral library. The sample is then quantified based on MS2 and/or MS1 level data.

Existing data analysis software, e.g. Spectronaut Pulsar (Biognosys AG) support many of the proposed data analysis workflows. The person skilled in the art will know which software to use or how to modify existing software to support the desired workflow.

In an exemplary peptide and/or protein quantification experiment employing DIA, the amount of the endogenous, unlabeled peptide variant relative to its labeled, reference peptide variant has to be determined. To this end, unlabeled and labeled peptides comprised in a sample are fragmented. Due to the label introducing only a small mass shift the fragment ions of both precursors will most often be present in the same combined fragment spectrum. Thus, only fragment ions differing in at least one label can be distinguished between unlabeled and reference peptide. The amount of unlabeled peptide relative to reference peptide can be determined by comparing the SRM-like peaks formed by these fragment ions differing in at least one label.

DIA methods have several advantages over DDA and other targeted methods such as SRM: DIA approaches have excellent sensitivity and a large dynamic range. Moreover, since no stochastic peak picking is involved DIA methods avoid the missing peptide ID data points typical for DDA methods and peptides are reproducibly measured over all samples. Furthermore, DIA allows sequencing of almost complete proteomes within one run without requiring prior knowledge about targeted transitions. All these properties make DIA methods especially suitable for quantification studies where many peptides and/or proteins need to be measured.

Figure 4:
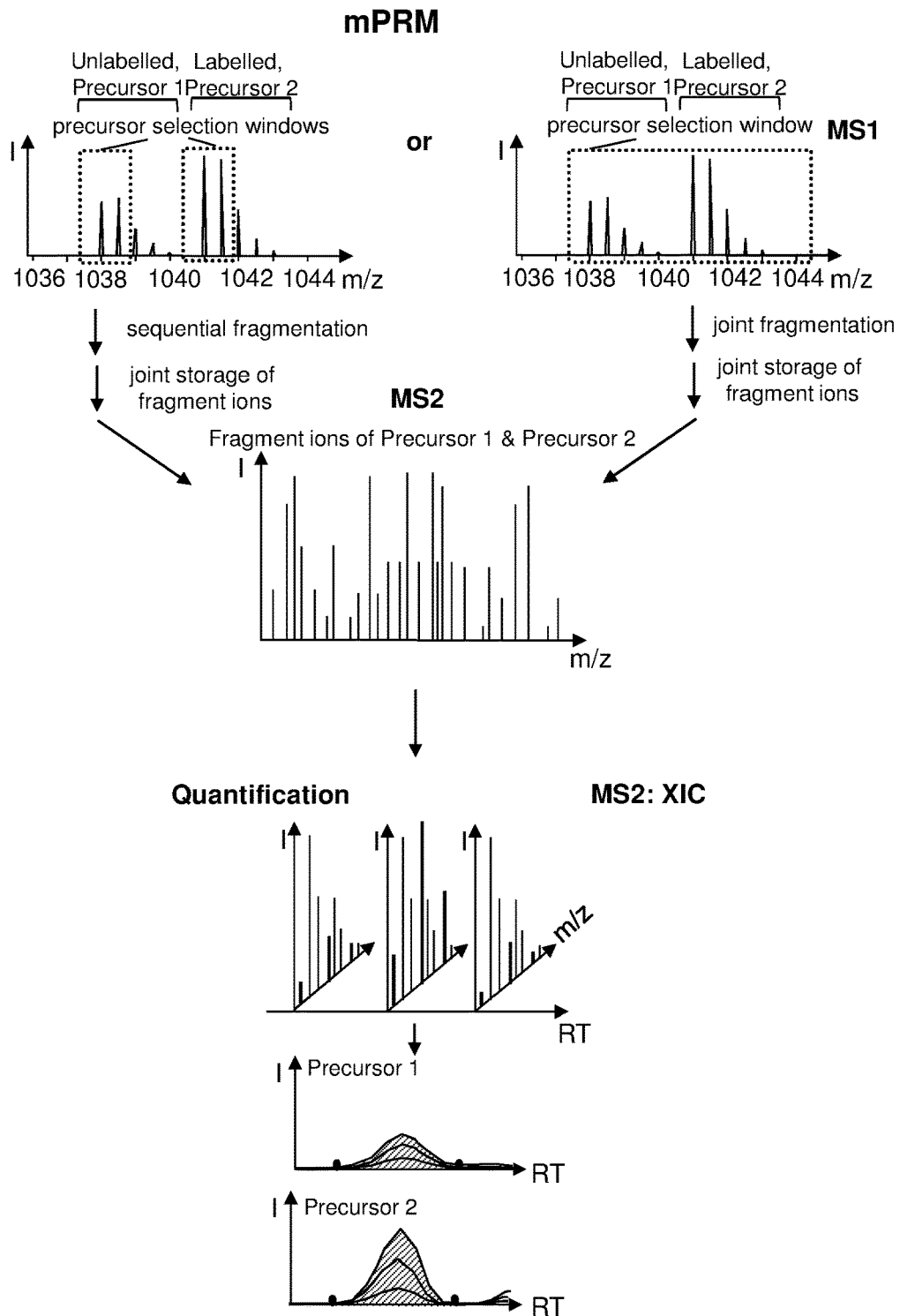
FIG. 4 shows a schematic drawing of an mPRM experiment, wherein either larger mass windows containing several precursors or several mass windows containing precursors are fragmented and the resulting data are stored together.

Another MS method which is frequently used for the quantification of peptides and/or proteins is Selected Reaction Monitoring (SRM). SRM is a targeted mass spectrometry approach. Herein, fragment ions of a single, preselected target peptide are detected on low resolution, low mass accuracy mass spectrometers. Only limited numbers of peptides can be monitored with this technique, and assay development is laborious. Multiplexed parallel reaction monitoring (mPRM), a novel targeted proteomics technique, remedies these disadvantages (FIG. 4).

Usually, mPRM analyses are conducted on a quadrupole which is combined with a high resolution mass analyzer. The quadrupole acts as mass filter to target mass ranges for fragmentation in a second quadrupole, and the resulting fragment ions are acquired by the high resolution mass analyzer. Fragmentation is done by either of two ways: Several precursors can be fragmented sequentially and their fragment ions are stored together for later measurement. Alternatively, larger m/z ranges containing several precursors are fragmented together. In both cases the fragmentation procedure results in combined fragment ion spectra comprising fragment ions from several precursors.

The fragment ions are analyzed in the high resolution part of the instrument, often an orbitrap analyzer. This has several advantages over using a low resolution instrument as in SRM studies: Firstly, all fragment ions a peptide produces can be monitored, rather than just a small number, leading to a higher specificity and increasing the confidence that the correct peptide was identified. Moreover, assay optimization becomes less crucial and the larger number of fragment ions that is monitored per peptide makes quantification more robust. Secondly, since the fragment ions are acquired with high resolution and mass accuracy, the probability of false positive identifications decreases.

DIA and mPRM workflows produce similar combined fragment ion spectra and can sometimes even be run on the same type of mass spectrometers. Therefore, also the basic principles for data analysis and quantification are the same. Thus, also for mPRM the SRM-like peak groups extracted from the fragment ion spectra can be used to quantify e.g. an unlabeled endogenous peptide versus a labeled reference peptide. Hence, quantification in an mPRM experiment is usually done based on MS2 level data.

The advantages of mPRM over DDA and SRM are similar to the ones mentioned above for DIA: high sensitivity, a large dynamic range, and reproducible peptide picking. As a consequence, it is especially suitable for quantification studies.

The present invention solves the problem of fragment overlap for any method that produces combined fragment ion spectra. This includes mass spectrometry methods acquiring low resolution data that is stored as combined fragment ion spectrum. Moreover, mass transmission windows for selecting precursors for fragmentation can be non-overlapping, overlapping, and/or can be sliding windows with small offsets. One DIA method using the latter is SONAR (Waters). This technique uses a quadrupole that slides over a selected mass range during each MS scan using transmission mass windows with offsets of a few Daltons. One full scan covers the whole mass range and high and low collision energy are applied in an alternating fashion to the scans, thus producing both MS1 and MS2 data. The person skilled in the art will know how to set up and operate the corresponding mass spectrometry setting.

Combined fragment ion spectra can be produced by pooling data of fragment ions from several precursors in one transmission mass window, e.g. as described in the examples. Even DDA methods can thus produce combined fragment ion spectra if large transmission mass windows are used and several precursors are fragmented together. Alternatively, fragment ion data of precursors from different transmission mass windows can be pooled to form a combined fragment ion spectrum. This principle is for example used in multiplexed DIA (Egertson, J. D., MacLean, B., Johnson, R., Xuan, Y., and MacCoss, M. J., 2015. Multiplexed Peptide Analysis using Data Independent Acquisition and Skyline, Nature Protocols, 2015, 10(6), pp. 887-903.). The person skilled in the art will know how to set up the corresponding mass spectrometry acquisition methods. Data analysis of the combined fragment ion spectra proceeds as described.

Figure 5:
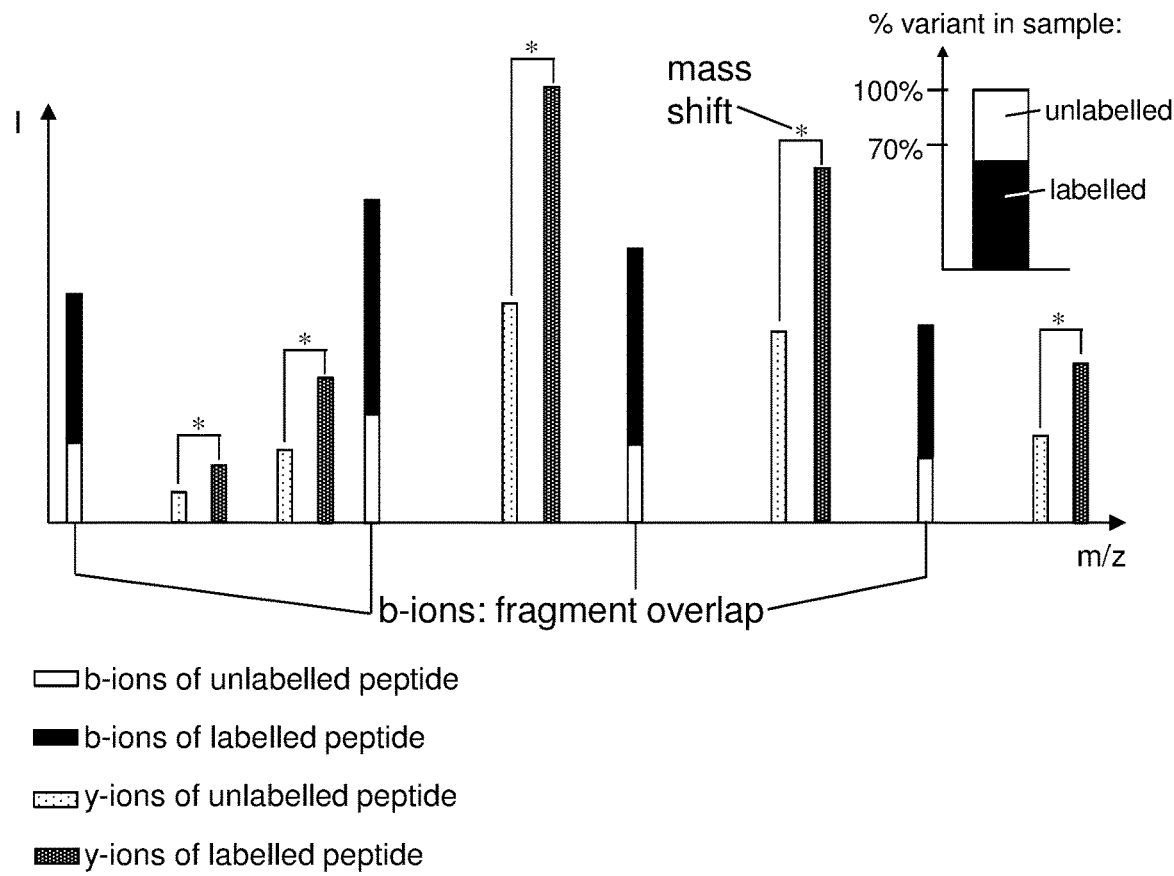
FIG. 5 shows a) fragment overlap for unlabeled peptides and peptides with a single heavy label and b) displays a schematic drawing of the y- and b-ions.
Figure 5:
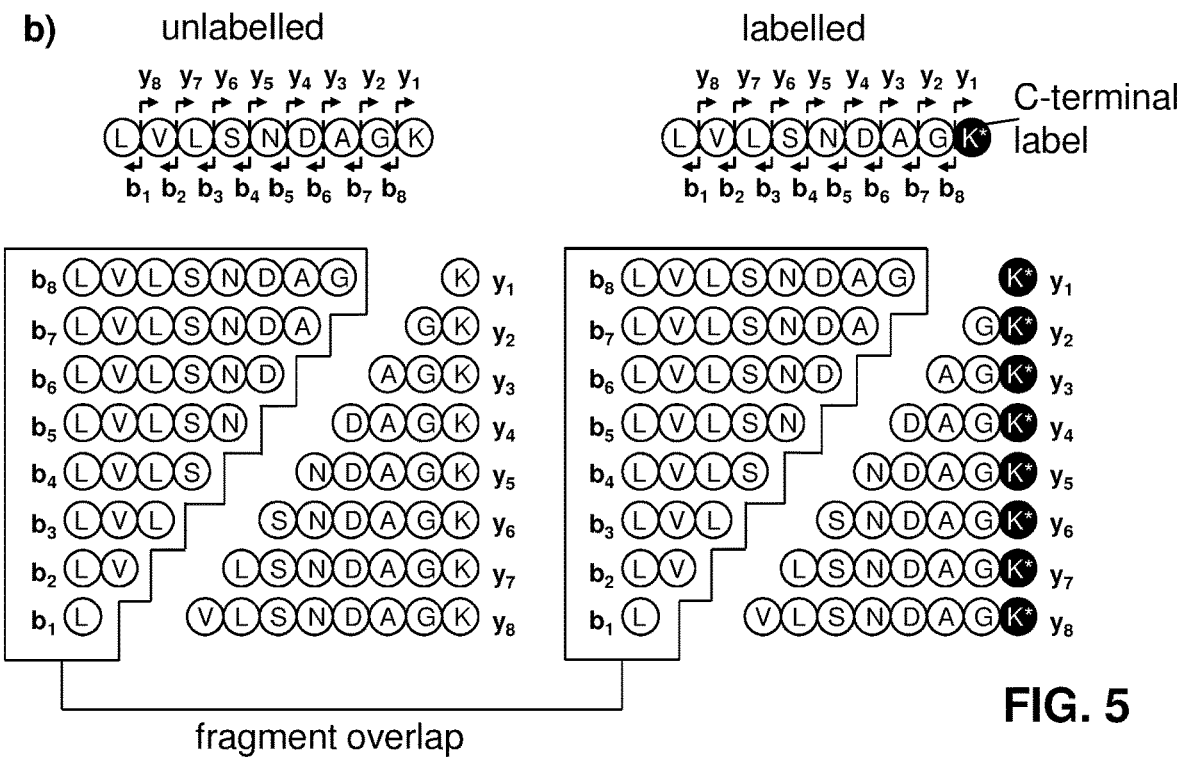
Figure 13:
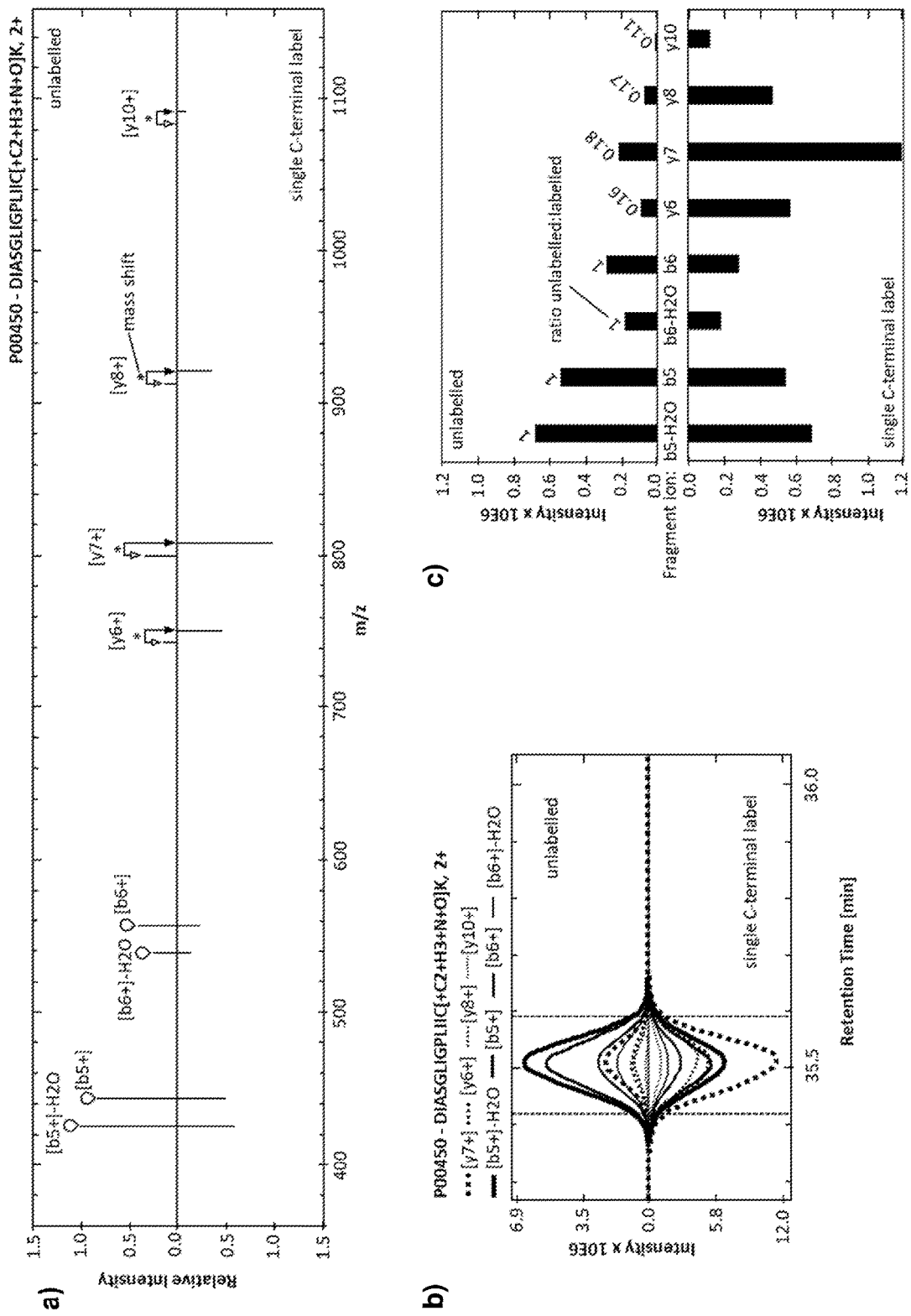
FIG. 13 shows a) a combined fragment ion spectrum acquired with mPRM comprising fragment ions from the unlabeled and the single-labeled variant of peptide DIASGLIGPLIIC[+C2+H3+N+O]K, b) the fragment ion traces for fragment ions from the unlabeled and the single-labeled variant of peptide DIASGLIGPLIIC[+C2+H3+N+O]K, and c) a barplot depicting fragment-ion intensities for the unlabeled and the single-labeled variant of peptide DIAS GLIGPLIIC[+C2+H3+N+O]K and the fragment ion intensity ratio between the two variants. The code [+C2+H3+N+O] denotes a carbamidomethyl modification at cysteine that is typically introduced on purpose during sample preparation.
Figure 15:
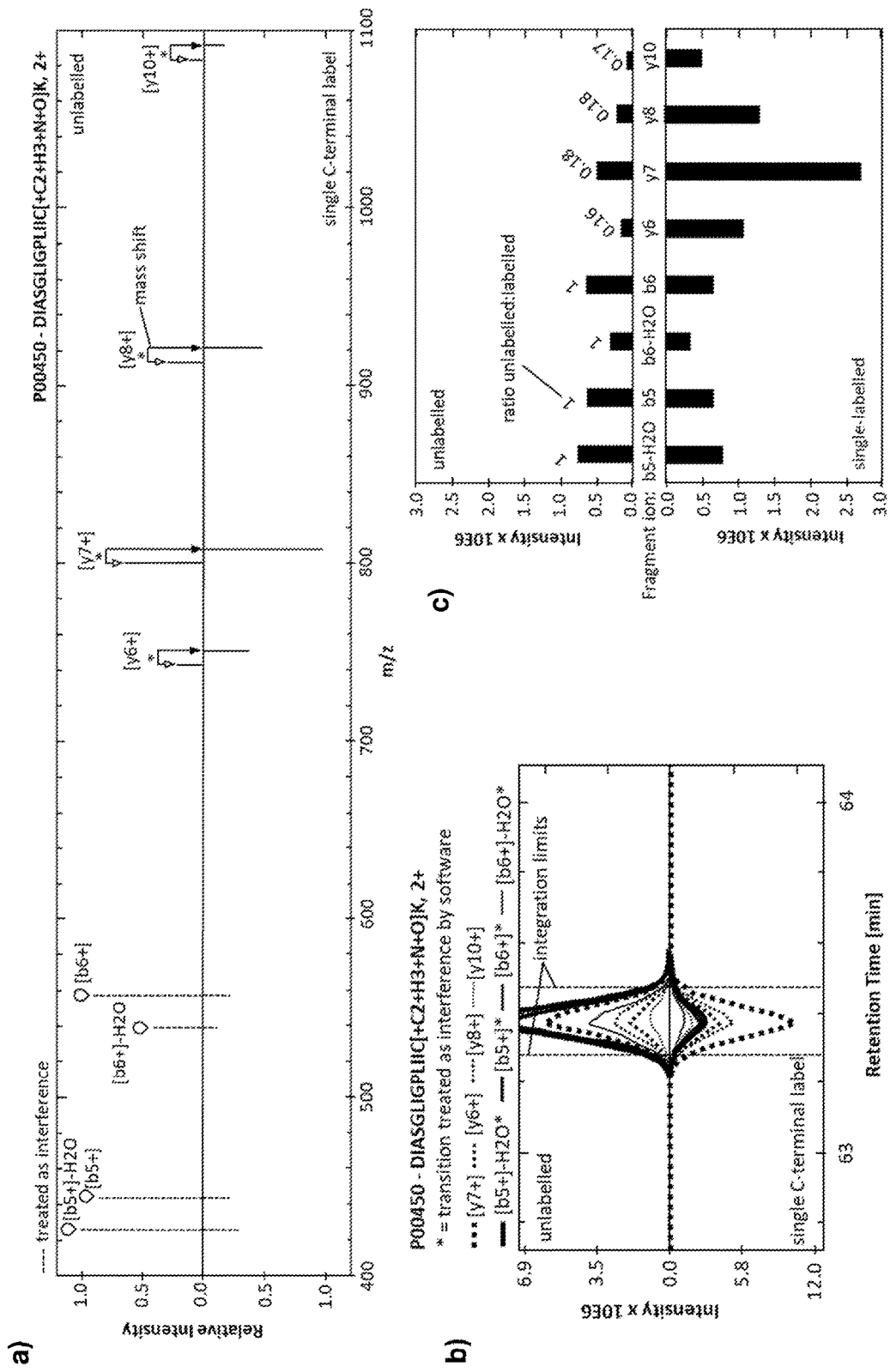
FIG. 15 shows a) a combined fragment ion spectrum acquired with DIA comprising fragment ions from the unlabeled and the single-labeled variant of peptide DIASGLIGPLIIC[+C2+H3+N+O]K, b) the fragment ion traces for fragment ions from the unlabeled and the single-labeled variant of peptide DIASGLIGPLIIC[+C2+H3+N+O]K, and c) a barplot depicting fragment-ion intensities for the unlabeled and the single-labeled variant of peptide DIASGLIGPLIIC[+C2+H3+N+O]K and the fragment ion intensity ratio between the two variants. The code [+C2+H3+N+O] denotes a carbamidomethyl modification at cysteine that is typically introduced on purpose during sample preparation.
Figure 16:
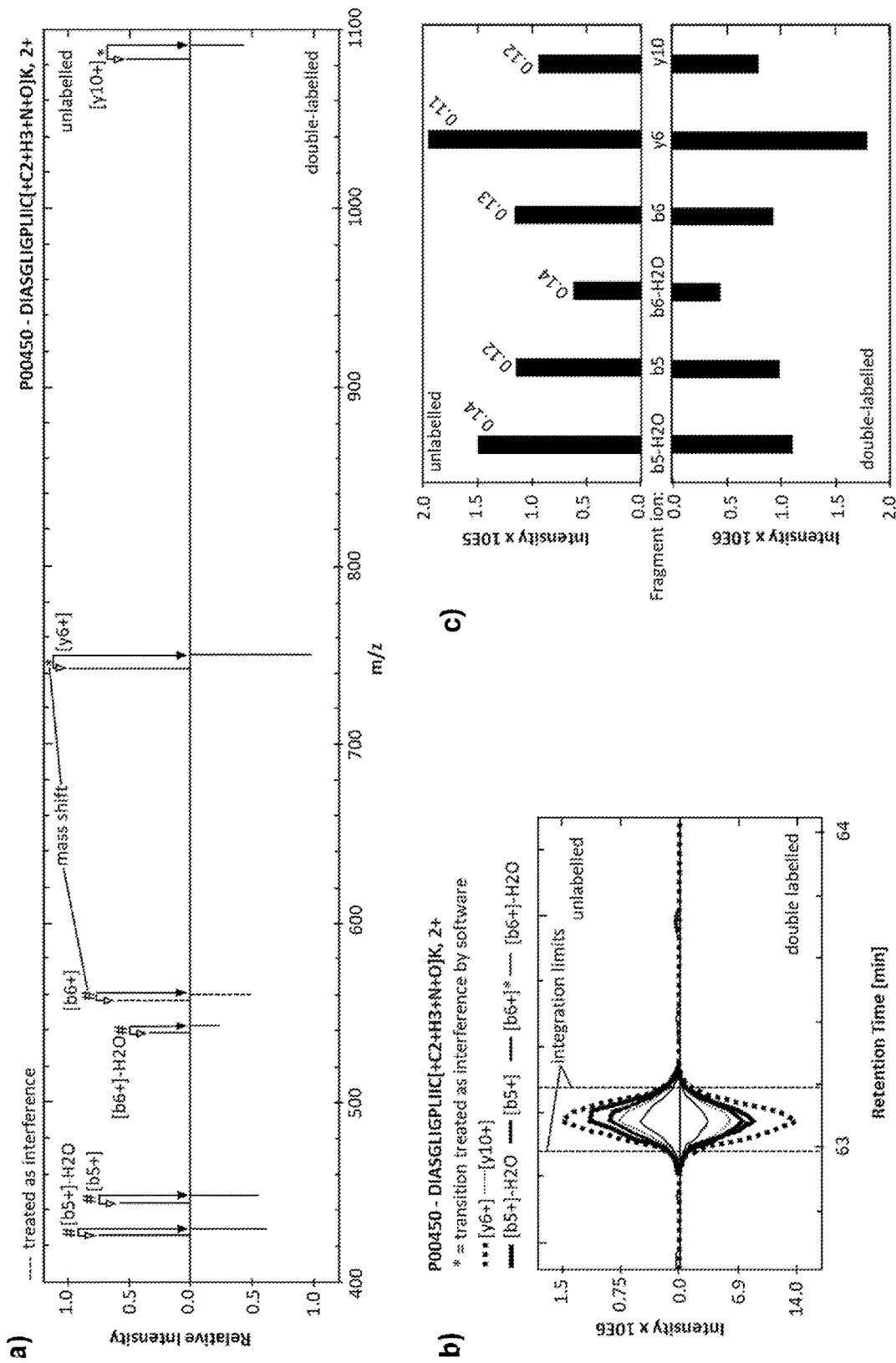
FIG. 16 shows a) a combined fragment ion spectrum acquired with DIA comprising fragment ions from the unlabeled and the double heavy-labeled variant of peptide DIASGLIGPLIIC[+C2+H3+N+O]K, b) the fragment ion traces for fragment ions from the unlabeled and the double heavy-labeled variant of peptide DIASGLIGPLIIC[+C2+H3+N+O]K, and c) a barplot depicting fragment-ion intensities for the unlabeled and the double heavy-labeled variant of peptide DIASGLIGPLIIC[+C2+H3+N+O]K and the fragment ion intensity ratio between the two variants. The code [+C2+H3+N+O] denotes a carbamidomethyl modification at cysteine that is typically introduced on purpose during sample preparation.

Use of Multiply-Labeled Peptides in Quantification Studies Employing DIA or mPRM:

A common setup for protein and/or peptide quantification is to compare the abundances of an unlabeled, endogenous peptide and its reference peptide variant carrying a single C-terminal label. Usually, this is an amino acid containing heavy elemental isotopes, most commonly arginine or lysine. When a combined fragment spectrum of these peptides is acquired with DIA or mPRM the presence of a single label will lead to complications: All C-terminal ions from the reference peptide will contain the label and will have an m/z distinct from their unlabeled counterparts (FIGS. 5a, 5b). However, N-terminal ions from the reference peptide, such as b-ions, will not contain any label and will have the same m/z as the corresponding ions from the unlabeled peptide (FIGS. 5a, 5b). We call this "fragment overlap". As a consequence, none of the N-terminal fragment ions can be used for quantification. Only the C-terminal fragment ion pairs differing in one label will reflect the abundance ratio between the unlabeled and the reference peptide. The use of only roughly half of the theoretical fragments leads to a less robust quantification. To further aggravate the problem, the presence of shared fragments between two peptide variants further complicates data analysis and hampers peptide identification, for instance if the known relative fragment ion intensity is used for scoring. The relative fragment ion intensities are the intensities of fragment ions within one peptide variant's peak. An example would be if for an unlabeled peptide b7 is the most intense ion, followed by y10, and y5. The relative fragment ion intensities follow a certain pattern for each peptide sequence, usually regardless of the label. Therefore, they can be used in the identification of both, unlabeled and labeled, peptides. If reference peptides are used that produce fragment overlap with the peptide variants to be quantified, the relative fragment ion intensities for both peptide variants might be skewed (FIG. 13, FIG. 15). Thus, fragment overlap can impair peptide and/or protein identification.

Figure 6:
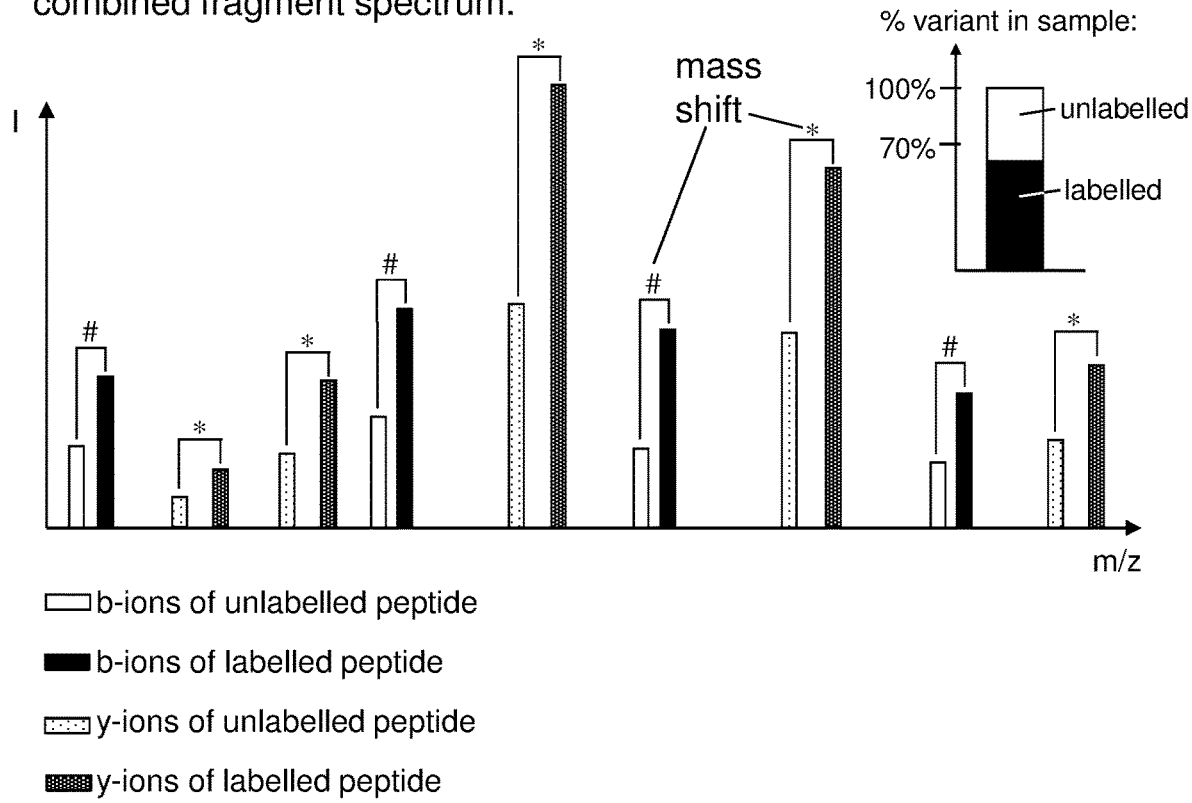
FIG. 6 shows a) a fragment ion spectrum without fragment overlap and b) displays a schematic drawing of the y- and b-ions for unlabeled peptides and double-heavy-labeled peptides.
Figure 6:
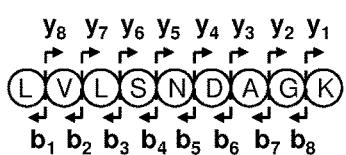
Figure 6:
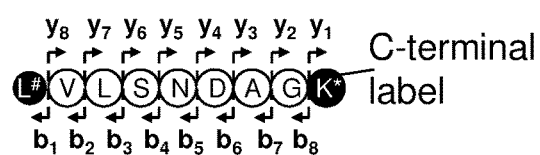
Figure 6:
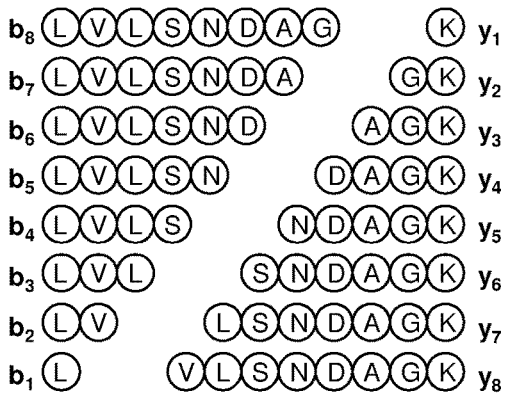
Figure 6:
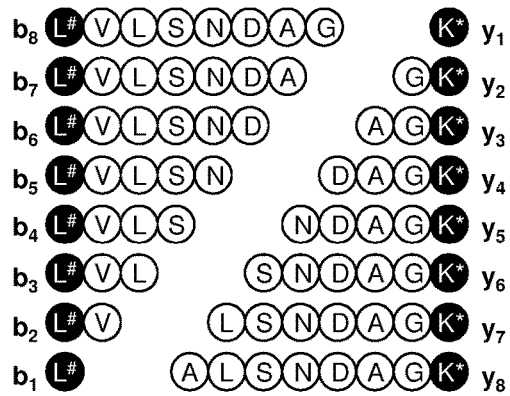

One way to eliminate the fragment overlap during DIA- or mPRM-based peptide and/or protein quantification experiments is by selectively introducing two labels (heavy isotope containing amino acids) at different positions into the reference peptides such that most C-terminal, as well as N-terminal fragments of interest will contain a label (FIG. 6). In any case the presence of multiple labels at suitable positions in the reference peptide results in distinct m/z for fragment ions from the reference and the unlabeled peptide (FIG. 6b), both for N- and C-terminal fragment ions. Thus, no fragment overlap occurs and the fragments stemming from unlabeled and labeled peptides can be distinguished.

The present invention makes use of such multiply-labeled reference peptides and/or proteins to provide an improved quantification method that is compatible with combined fragment ion MS spectra. Secondly, the present invention relates to a method for selecting the label and label position of at least one suitable reference peptide. Thirdly, the present invention relates to selectively double-labeled reference peptides for use in or produced by the above mentioned methods.

Using such multiply-labeled reference peptides solves the problems occurring with single-labeled reference peptides in conjunction with mass spectrometry approaches producing combined fragment ion spectra. It allows exploiting the full potential of DIA and mPRM methods for quantitative studies. Firstly, combined fragment ion spectra of unlabeled and labeled precursors will contain less shared fragment ions which can facilitate the identification of peptides and peak groups. For example, fragment overlap between reference peptides and peptides to be quantified might lead to skewed relative fragment intensities for both variants, as discussed above. Relative fragment intensities are often used for peptide and peak group identification and scoring. Therefore, using reference peptides that differ in at least 2 labels from the other peptide variant can aid peptide and/or protein identification.

Secondly, being able to differentiate between N-terminal fragment ions, such as b-ions, from unlabeled and from labeled peptides allows including them for quantification without skewing quantitative values. Including a higher number of suitable ions will render quantification more robust and accurate.

Steps for peptide and/or protein quantification using DIA or mPRM:

In quantification experiments unlabeled endogenous peptides and/or proteins will be pooled with reference peptides. Since sample preparation can introduce considerable inter-sample variability, preferably the unlabeled peptides and/or proteins and the labeled peptides are pooled as early as possible in the protocol. Thus, any variability introduced by later sample preparation steps will affect both, light and heavy peptide, in equal measures. The steps at which pooling is most suitable may vary and are therefore not included in the standard protocol below. Most frequently, synthetic reference peptides are added to peptide samples in a last step before liquid chromatography.

A standard protocol for the quantification of peptides and/or proteins by DIA or mPRM mass spectrometry includes, but is not limited to, the following steps:

1. Protein extraction: Proteins are extracted from samples. If necessary, this can include the use of detergents, mechanical force, heat, chaotropes or other means. The suitable protein extraction protocol depends on the sample and the skilled person will know which one is suitable for a specific mixture.

2. Reduction of disulfide bonds: Prior to digestion disulfide bonds between cysteine residues of proteins, are reduced. This serves to make more residues accessible for digestion and prevents two peptides from being connected which would result in complex fragment ion spectra. Preferably, Dithiothreitol (DTT) or TCEP (Tris(2-carboxyethyl) phosphine hydrochloride) are used for this step.

3. Alkylation of free cysteines: In order to avoid re-formation of disulfide bonds the free cysteines are alkylated, preferably with iodoacetamide or iodoacetic acid. The reaction is carried out in the dark to avoid formation of side products and further modifications.

4. Protein digestion: Proteins in the sample are cleaved into peptides, preferably using a protease such as trypsin and/or Lys-C. The reaction is preferably carried out at 37° C. in a suitable buffer.

5. Peptide purification: The peptides are purified prior to MS analysis. Preferably they are desalted, typically using a C18 stationary phase.

6. Liquid chromatography: Several microliters of sample are loaded onto a liquid chromatography column and are separated, preferably by increasing hydrophobicity via reversed-phase LC and a gradient of increasing acetonitrile concentrations.

7. MS analysis: Peptides elute, are ionized and subjected to MS analysis via either a DIA- or an mPRM-method. Fragment ions are detected on a high resolution instrument and combined fragment ion spectra are stored.

8. Data analysis: Quantification is usually done based on MS2 level data. Spectra can be searched against a spectral library, or theoretical spectra, or can be mined using SRM-like transitions to identify and quantify peptides and/or proteins. Examples for specialized software for these analyses are Spectronaut and Spectronaut Pulsar (Biognosys AG), DIA-Umpire (Tsou, C. C., Tsai, C. F., Teo, G., Chen, Y. J., Nesvizhskii, A. I., 2016. Untargeted, spectral library-free analysis of data independent acquisition proteomics data generated using Orbitrap mass spectrometers. *Proteomics*, (15-16), pp.2257-2271.) or OpenSWATH. Fragments from the same peptide are subsequently arranged in SRM-like peak groups: The signal corresponds to the intensity of each fragment monitored over time in sequential spectra. Fragments of the same peptide will produce similarly shaped elution peaks with maxima at identical retention times (RT). These SRM-like peak groups can then be used to quantify e.g. an unlabeled endogenous peptide versus a labeled reference peptide. Alternatively, data analysis approaches which do not rely on DDA-based spectral libraries, or do not rely on them exclusively, can be applied for peptide and/or protein identification and/or quantification. Analysis software, such as Spectronaut Pulsar, support these data analysis workflows. Moreover, quantification can be done on MS1 and/or MS2 level. The details and the optimal implementation of the standard protocol depend on the purpose of the experiment, the properties of the sample and the proteins of interest, and the instruments used, among other factors. The skilled person will know how to implement and alter the standard workflow to best suit a specific setup.

The following paragraphs guide through the details of selecting a suitable label and label position for selectively double-labeled reference peptides:

To produce double-labeled reference peptides, the labels are introduced selectively at certain positions within the peptide sequence. The label position is crucial to ensure an optimal balance between the information content provided (which is biggest for terminal labels) and other parameters, e.g. total label cost. Therefore, the present invention relates to a method for selecting the label and label position of at least one suitable reference peptide. A method for the selection of optimal label positions to produce double-labeled peptides can for example contain the following steps (FIG. 7):

In a first step, a spectral library is selected. Moreover, any additional input data required for the optimization according to the desired parameters will be supplied. E.g. if the optimization occurs according to total label cost, the label cost for each label is obtained. In addition, the label positions to be considered during the optimization process need to be defined. This includes how many amino acid positions within the terminus will be considered, as well as if both termini of the peptide will be optimized according to the same parameters.

In a second step, the most advantageous amino acid position for labeling within the considered amino acids is determined for each peptide in the spectral library. During this step different parameters can be balanced to find the optimal label, e.g. information content of labeled fragment ions, total label cost which reflects the availability of the label and the complexity of its incorporation etc. For the optimization according to total label cost, the label with the lowest label cost but yielding fragment ions with maximum information content would be selected.

Optionally, the method could further include any of the following features:
- an estimation of the total label cost for the selected labels and label positions,
- a simulation of fragment collisions,
- a calculation of label and label position frequencies,
- and/or a report of the results.

Figures 7, 8:
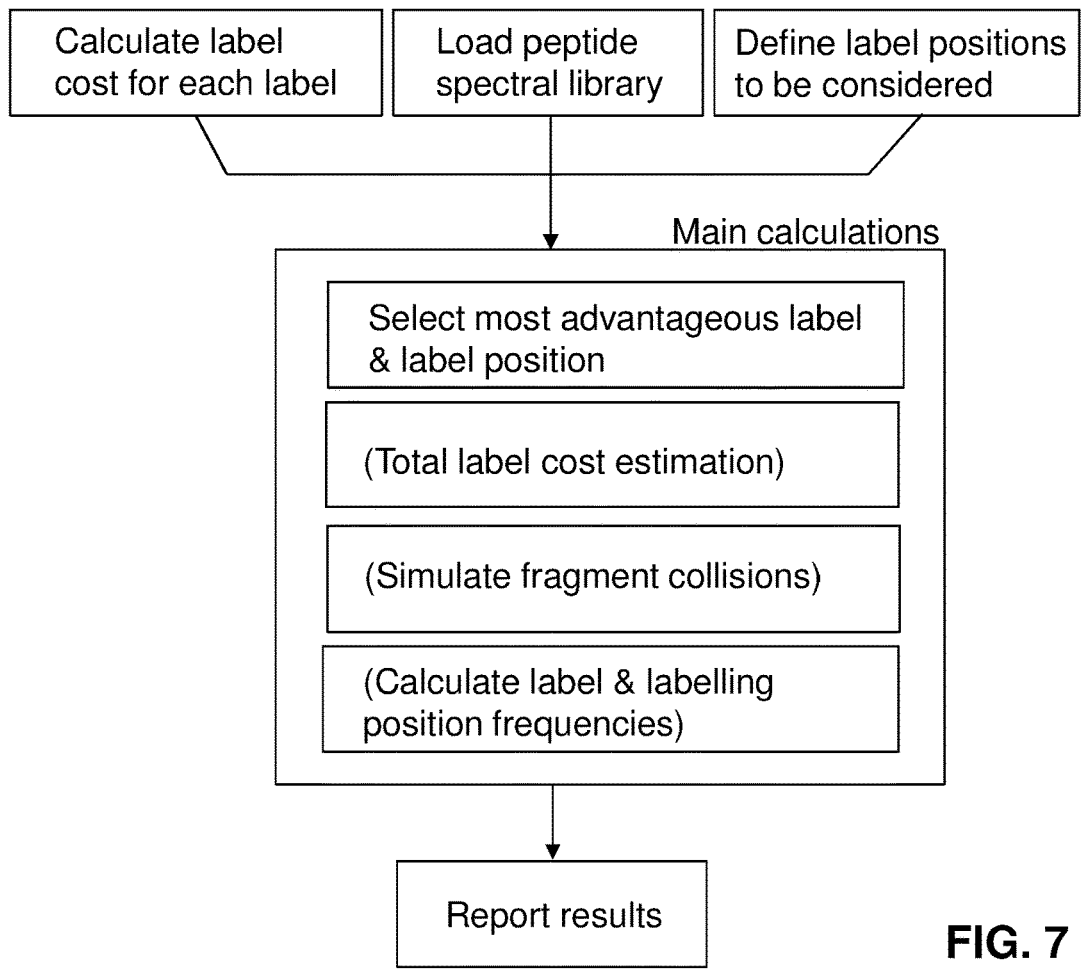
FIG. 7 exemplifies processes in a method to select optimal label positions.
FIG. 8 shows a schematic drawing of a calculation mode for selecting label positions.
Figure 9:
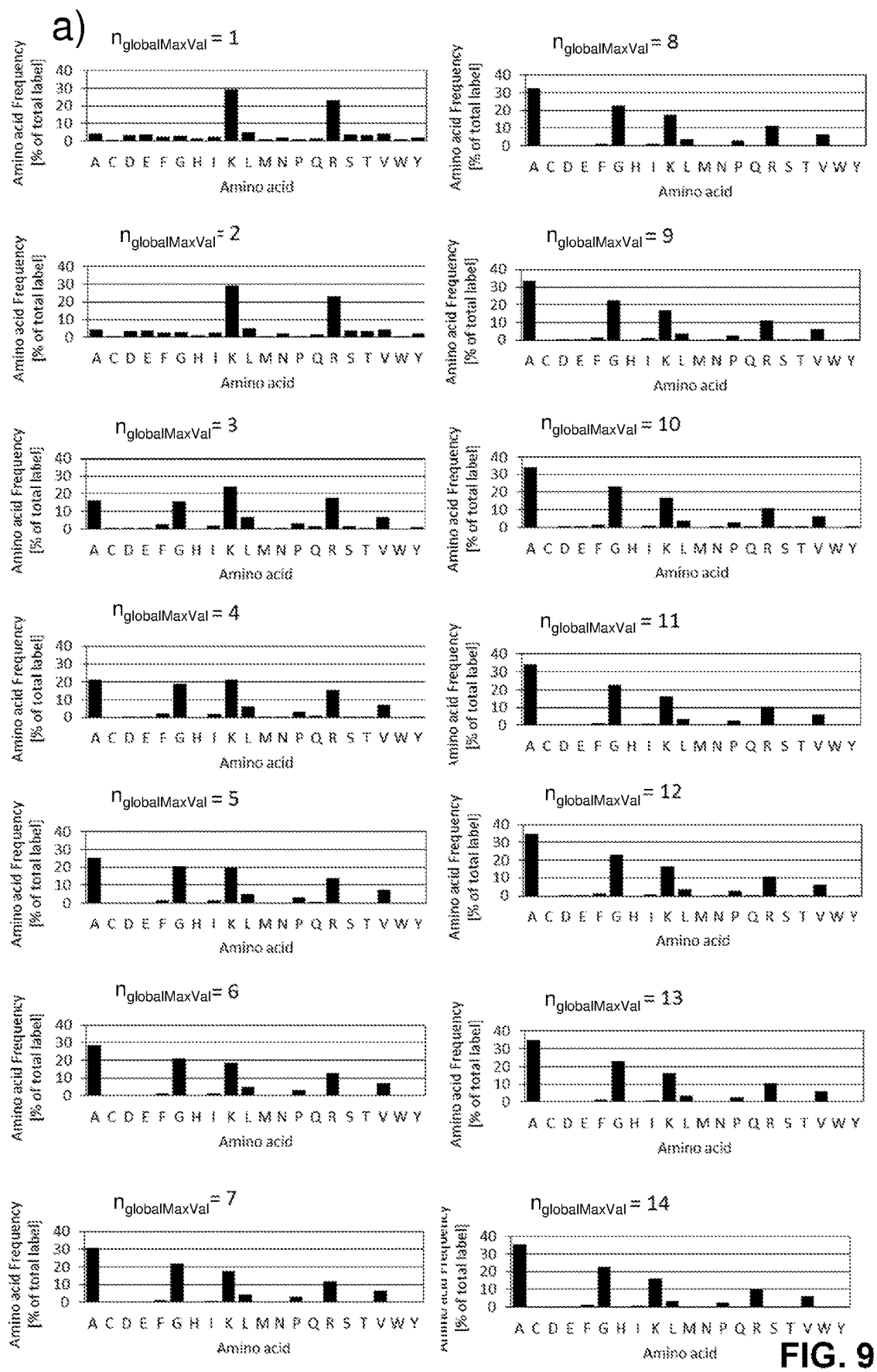
FIG. 9 in a) and b) exemplifies the outcome of an analysis for optimal label positions: barplots show the frequency with which each amino acid would be labeled for different $n_{globalMaxVal}$ and a human blood plasma peptide spectral library containing two isotopically labeled amino acids per peptide.
Figure 9:
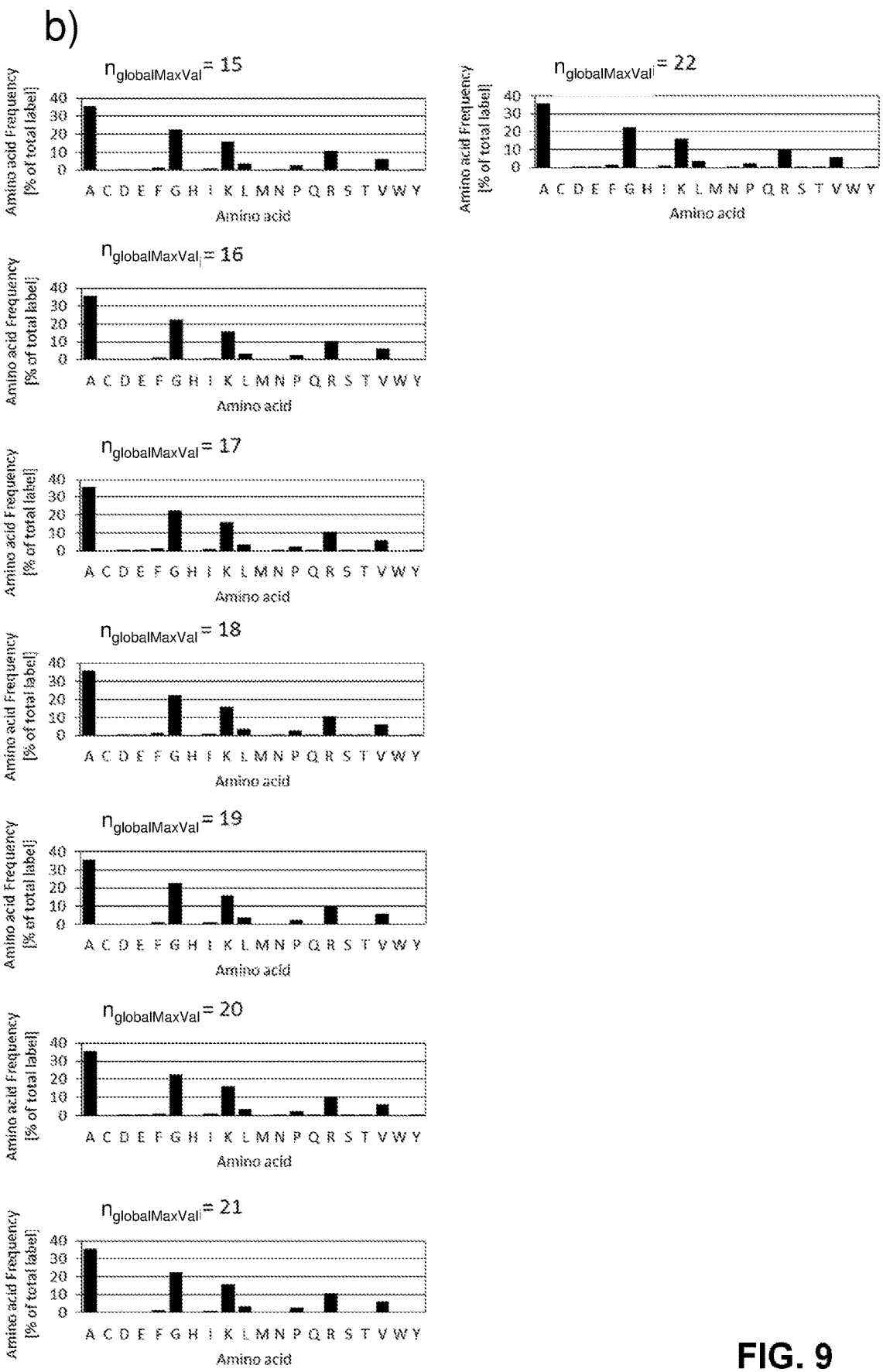

In FIG. 8 an example of a calculation mode for an optimal label position analysis according to total label cost is displayed. Further, non-limiting details are listed in Example 3. To produce double-labeled reference peptides based on a spectral library wherein the positions for the heavy amino acid labels are optimized according to total label cost, a list of the label costs for all labels is needed. When selecting the labels and label positions, amino acids within a selected number ($n_{globalMaxVal}$) of positions from each terminus are considered for labeling. If a peptide comprises less amino acids than the double of $n_{globalMaxVal}$ then instead all amino acids within $n_{pepMaxVal}$ positions from each terminus are considered for labeling, wherein $n_{pepMaxVal}$ corresponds to the peptide length divided by two and rounded down to the next lowest integer. For each peptide the amino acid with the lowest label cost will be selected from the stretch of considered amino acids ($n_i$). The label costs of all labels for each peptide will then be summed up to estimate the total label cost for the specific $n_{globalMaxVal}$. If the positioning of the labels is optimized according to a specific parameter, then the amino acids with the best "values" for the respective parameter should be preferred over other amino acids. As a consequence they are picked more frequently for labeling. FIG. 9 illustrates this: Optimal label positions were analyzed for double-labeling all peptides in a human plasma spectral library with amino acids containing heavy elemental isotopes. The label positions were optimized according to lowest label cost, e.g. the labeled amino acid with the lowest price per millimole from a certain vendor were preferred. This in turn also results in the lowest total label cost, i.e. the price for all labels used to label a certain amount of a specific set of proteins and/or peptides with a specific $n_{globalMaxVal}$. The character "$n_i$" denotes the length of terminal amino acid stretches that were considered for positioning the label. E.g. "$n_i$=4" indicates that a first label can be incorporated at the position of any the 4 most N-terminal amino acids, and a second label can be incorporated at the position of any of the 4 most C-terminal amino acids. The frequency with which each amino acid was picked for labeling all peptides of the spectral library is displayed for $n_{globalMaxVal}$ values from 1 to 22 (with 22 corresponding to half the length of the longest peptide in the library, rounded down to the next integer). The longer the $n_{globalMaxVal}$, the more positions are considered for labeling and the closer a situation is approached where primarily label positions are picked which correspond to alanine, glycine, arginine, leucine, arginine, and valine (FIG. 9). These are the five amino acids with the lowest label cost in this specific analysis.

Furthermore, we discovered that for the analysis displayed in FIG. 9, the decrease in total label cost was considerable for $n_{globalMaxVal}$ equal to 2, 3, 4, and 5. For higher $n_{globalMaxVal}$ the additional savings became smaller and a higher loss of information content occurred due to small fragment ions not being considered in the analysis.

The reference peptides of the present invention can further carry post translational modification(s) (PTM(s)). The PTMs of interest can be of biological importance to study signaling cascades via protein phosphorylation for instance or to reflect the chemical treatment of the sample during sample preparation. These can be any modification occurring on peptides and/or proteins. Preferably PTMs are selected from phosphorylation, acetylation, methylation, sulfation, hydroxylation, lipidation, ubiquitylation, sumoylation, glycosylation, oxidation, and carbamidomethylation. Preferably, the post translational modification(s) occurs on peptides and/or proteins in nature, or is introduced as part of a standard sample preparation workflow, e.g. as described in this application. For example, carbamidomethylation of cysteines is commonly introduced during sample preparation by reducing disulfide bonds and alkylating residues with iodoacetamide. Other common post translational modifications that are introduced during sample preparation are e.g. carbamylation due to urea present in the sample, or methionine oxidation.

Labeled peptides and their unlabeled counterparts contain the same post translational modification(s) at the same position(s) to ensure that both peptide variants exhibit similar behavior during sample preparation and LC-MS analysis. Thus, the reference peptide corresponds to the unlabeled peptide as present in the sample including any modifications, but with the respective isotopically labeled amino acids. The present invention can be particularly useful for the analysis of peptides with post translational modifications for which only few fragment ions are available for quantification, e.g. phospho-peptides. By minimizing or eliminating fragment overlap we can ensure that available N-terminal and C-terminal fragment ions can be used for identification and quantification. In some cases only a single b- or y-ion differentiates between isoforms of phospho-peptides where e.g. the phosphorylation can occur on either of two neighboring amino-acids. In such instances the present invention enables the unequivocal assignment of the modified amino acid. Chemical synthesis of peptides is usually carried out by attaching amino acid building blocks to each other. To introduce an isotopically labeled amino acid, the building block comprises the amino acid containing the corresponding heavy isotopes. To introduce an amino acid carrying a post translational modification, the building block usually already comprises the amino acid and the PTM. Building blocks are most often introduced by coupling the carboxyl group of an amino acid building block to the N-terminus of the peptide being formed. Thus, chemical synthesis usually starts at a peptide's C-terminus and proceeds to its N-terminus. To avoid side reactions during peptide synthesis, some of the amino acid building block's reactive groups have to be protected. Therefore, the individual amino acid building blocks are reacted with protecting groups before they are added to the nascent peptide. Once the building block has been integrated into the peptide, its N-terminus is deprotected to allow for incorporation of the next amino acid. After the peptide is fully formed, any remaining protecting groups are removed.

Figure 11:
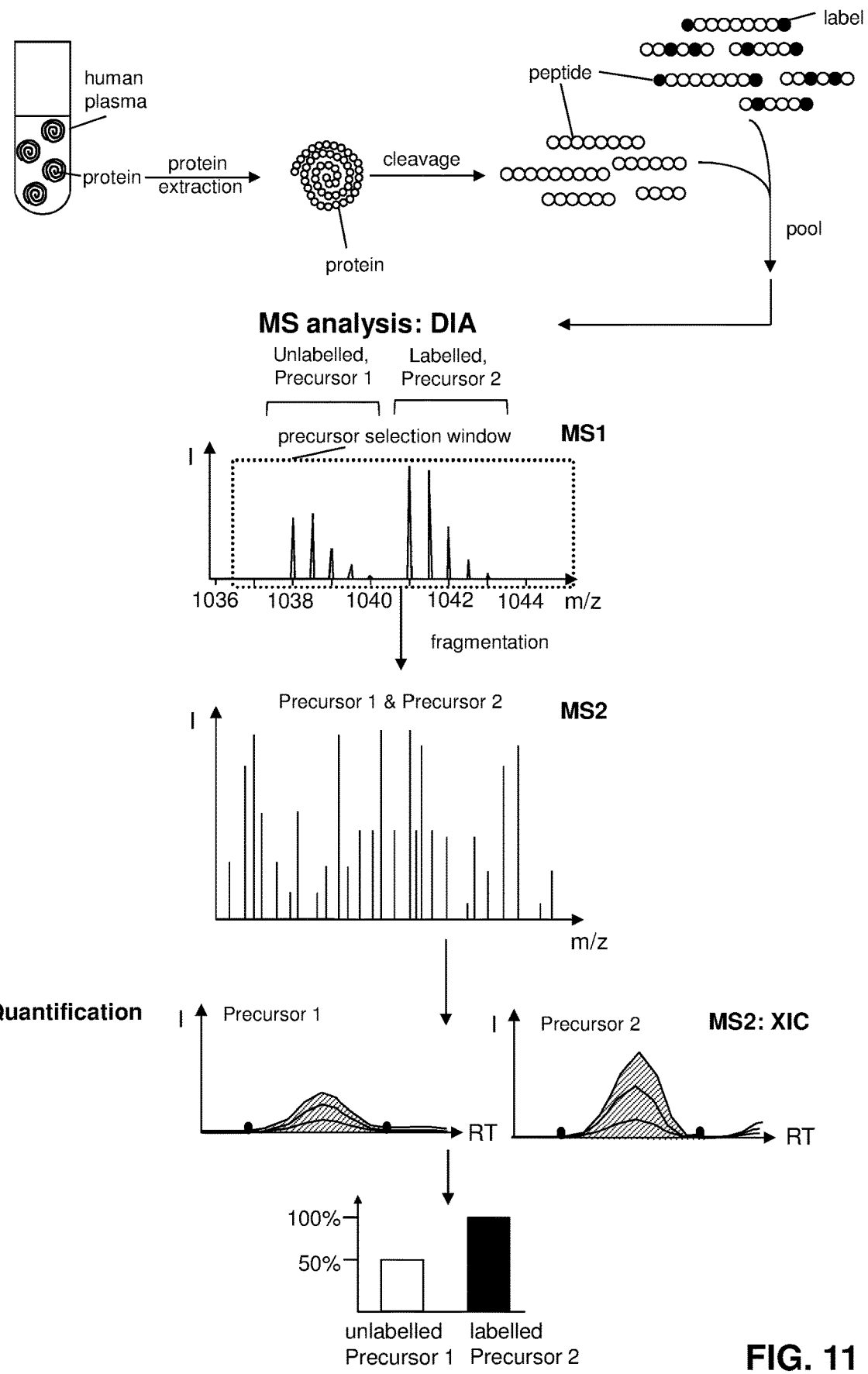
FIG. 11 shows a schematic drawing of an isotopic labeling experiment wherein labeled reference peptides are combined with an unlabeled peptide mixture and the acquisition method is DIA.
Figure 12:
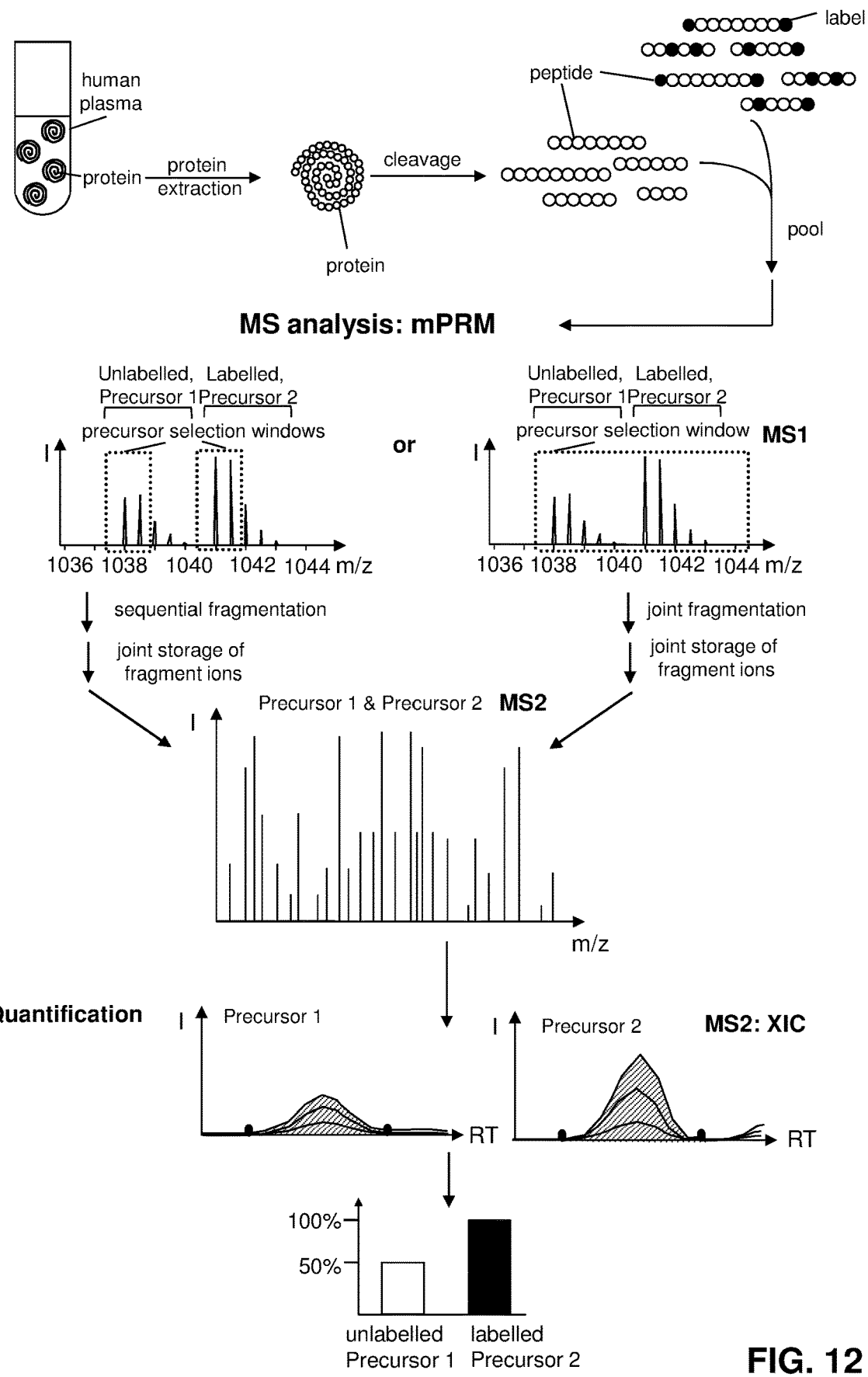
FIG. 12 shows a schematic drawing of an isotopic labeling experiment wherein labeled reference peptides are combined with an unlabeled peptide mixture and the acquisition method is mPRM.

Applications:

The methods and substances of the present invention can be applied to the quantification of a variety of samples, including different cell or tissue types, environmental samples, or bodily fluids. In a preferred embodiment the methods and substances of the present invention are applied to the quantification of human plasma proteins (FIGS. 10, 11, 12).

Figure 1:
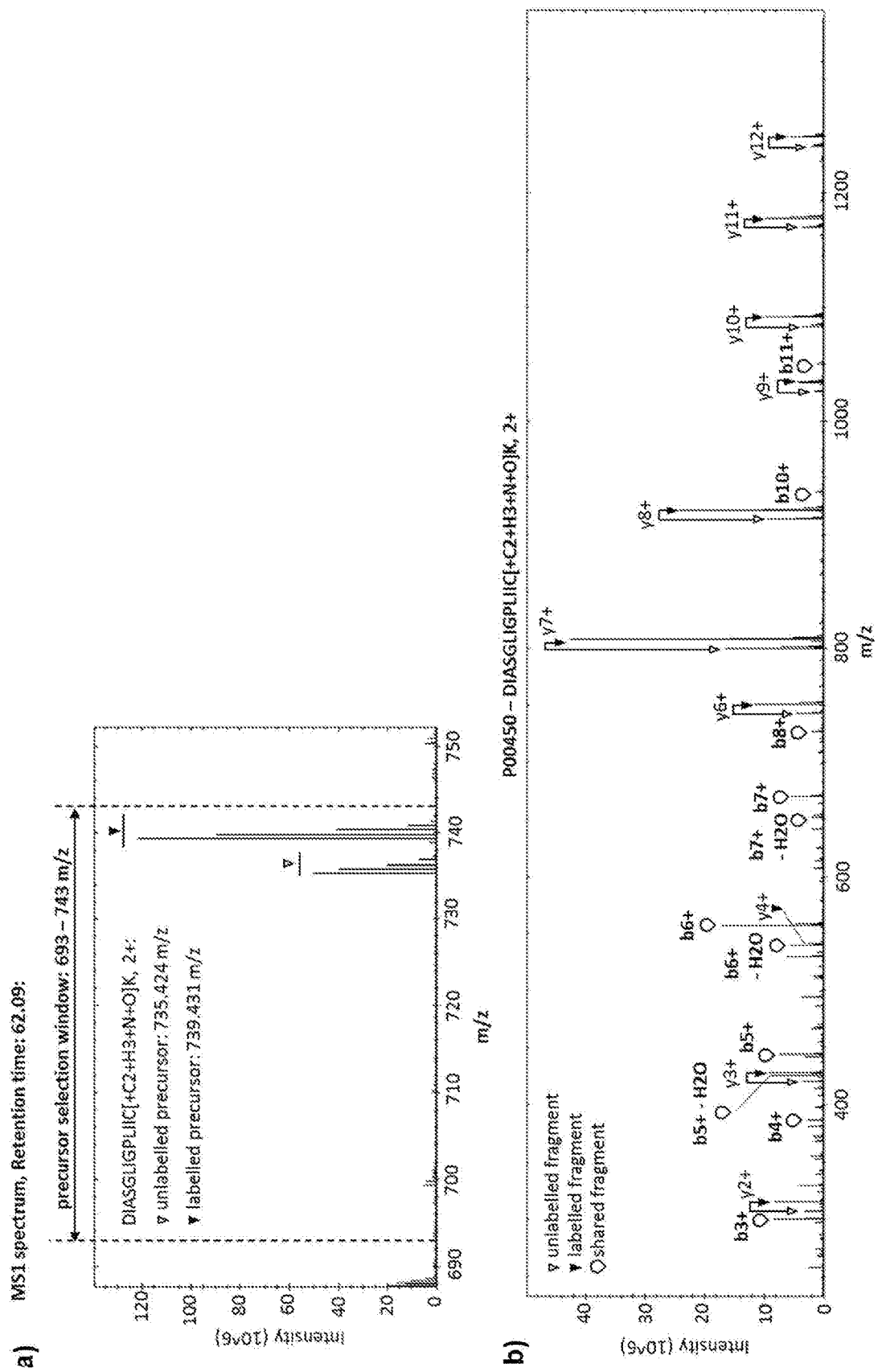
FIG. 1 shows a) an MS1 spectrum wherein the mass window for fragmentation containing the unlabeled and the labeled precursor is marked, and b) a combined fragment ion spectrum comprising fragment ions from the unlabeled and the single-labeled variant of peptide DIASGLIGPLIIC[+C2+H3+N+O]K. The code [+C2+H3+N+O] denotes a carbamidomethyl modification at cysteine that is typically introduced on purpose during sample preparation.
Figure 10:
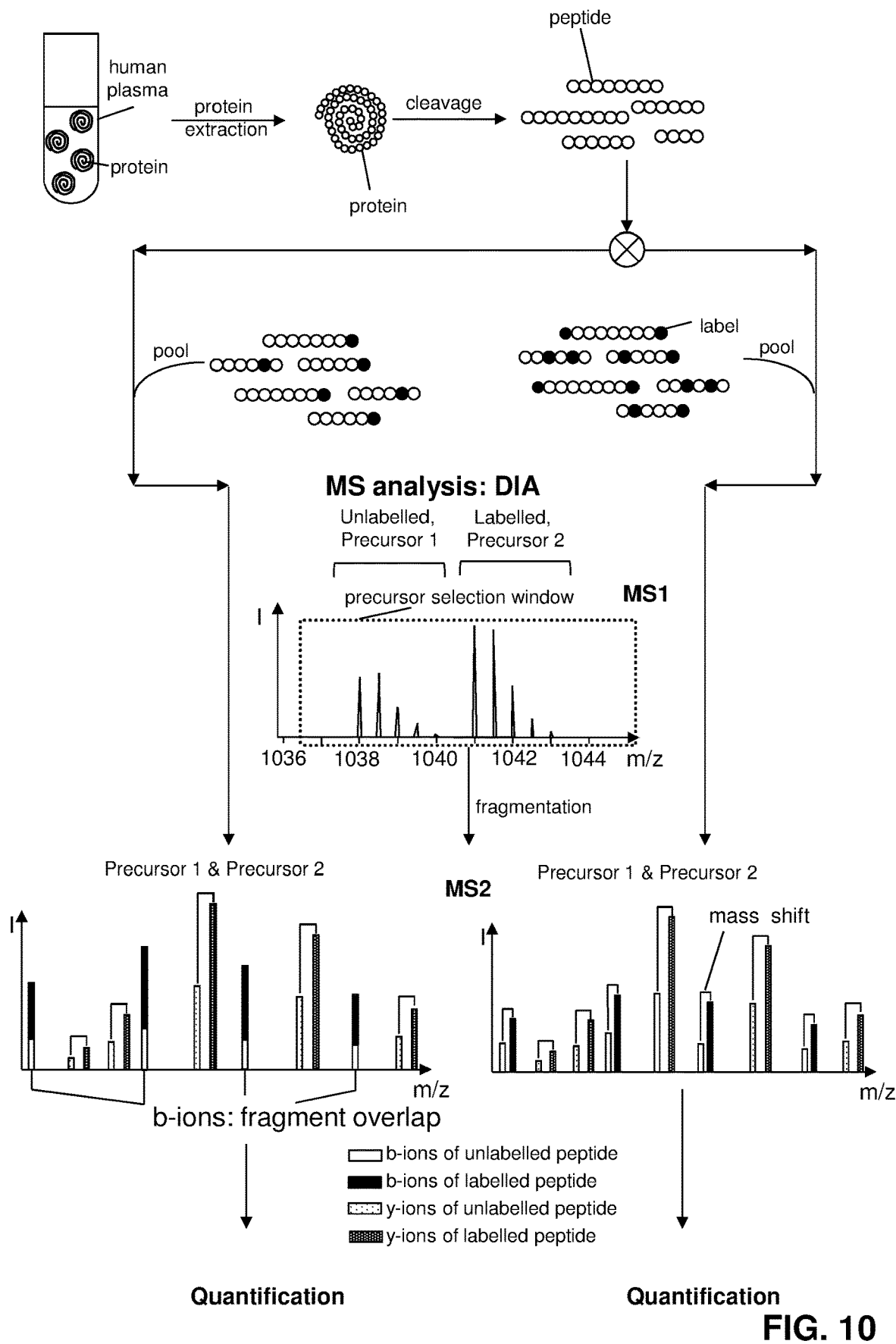
FIG. 10 shows a schematic drawing of an isotopic labeling experiment wherein either single- or double-labeled reference peptides are combined with an unlabeled peptide mixture and the acquisition method is DIA.

In a first aspect, we analyzed the fragment overlap occurring during DIA-based quantification of human plasma peptides and/or proteins with sets of single-labeled synthetic peptides (FIG. 1, FIG. 10). To this end human plasma was subjected to in solution digestion: 10 µl of plasma were diluted in 75 µl 10 M urea and 0.1 M ammonium bicarbonate. The samples were reduced with 5 mM TCEP for 1 h at 37° C. Subsequently, the plasma was alkylated with 25 mM iodoacetamide for 20 min at 21° C. The samples were diluted to 2 M urea and digested with trypsin at a ratio 1:100 (enzyme to protein) at 37° C. for 15 h. The samples were centrifuged at 20,000 g at 4° C. for 10 min. The peptides were desalted using C18 MacroSpin columns from The Nest Group according to the manufacturer's instructions. After drying, the peptides were resuspended in 1% ACN and 0.1% formic acid. Sets of reference peptides, each carrying a C-terminal heavy amino acid label (Arg10 or Lys8), were added to all of the samples. The reference peptides were derived from plasma protein sequences and thus allowed for the quantification of a number of endogenous plasma proteins.

Two micrograms of each sample were analyzed using a self-made analytical column (75 µm×50 cm length, packed with ReproSil-Pur 120 A C18-AQ, 1.9 µm) at 50° C. on an Easy-nLC 1200 connected to a Q Exactive HF mass spectrometer (Thermo Scientific). The peptides were separated by a 1 h segmented gradient from 1 to 52% acetonitrile (ACN) in 60 min with 0.1% formic acid at 250 nl/min, followed by a linear increase to 90% ACN in 2 min and 90% for 10 min. The DIA-MS method consisted of a survey scan at 120,000 resolution from 350 to 1,650 m/z (AGC target of $3*10^6$ or 60 ms injection time). Then, 14 DIA windows were acquired at 30,000 resolution (AGC target $3*10^6$ and auto for injection time) spanning 350-1650 m/z. Stepped collision energy was 10% at 27%. The spectra were recorded in profile mode. The default charge state for the MS2 was set to 4.

The spectra were processed to extract peptide and protein identifications and quantitative values using specialized software such as Spectronaut (Biognosys AG). To demonstrate the fragment overlap occurring in combined fragment ion spectra between N-terminal b-ions from endogenous, unlabeled peptide and single-labeled synthetic reference peptides, we further analyzed spectra from single peptides.

Combined fragment ion spectra for three peptides showing an intense signal were analyzed. FIG. 1 shows DIA data for one peptide present in an unlabeled, as well as a labeled variant carrying a modified lysine residue (K8) as single C-terminal label. In a first part of the Figure a section of an MS1 spectrum is displayed (FIG. 1a). The 50 Th mass window containing both the unlabeled and the labeled precursor of peptide DIASGLIGPLIIC[+C2+H3+N+O]K is marked (FIG. 1a). All ions inside this swath were fragmented and a combined fragment ion spectrum comprising fragment ions from both the unlabeled and the labeled peptide was acquired (FIG. 1b). The fragment overlap for different fragment ions was analyzed. Fragment ions from the unlabeled (light) precursor are marked with white triangles, fragment ions from the labeled (heavy) precursor are marked with black triangles, and shared b-ions are marked with pointed circles. A mass shift between corresponding fragment ions from unlabeled and labeled peptides due to the C-terminal label is displayed as a line connecting two triangles. All y-ions show such a mass shift (for y4+ the unlabeled signal is not marked). On the other hand, fragment overlap was observed for all b-ions in the spectrum. This affects quantification: if intensity at the apex of the first monoisotopic peak is compared, the y-fragment-ions have a light (unlabeled) to heavy (labeled) ratio (L/H ratio) <0.5 which reflects the ratio between the light and heavy precursor peptide in the MS1 spectrum (FIG. 1a). However, if b-ions are to be used for quantification, they show an L/H ratio of 1 since the same shared fragment ion peaks are compared between light and heavy peptides. Thus, if the b-ions are considered in the calculation they will skew the L/H ratios towards a higher amount of unlabeled peptide. Furthermore, due to the fragment overlap of b-ions spectra of light and heavy peptides comprise shared fragments. All these problems, fragment overlap leading to inaccurate quantitative values or unused ions and shared fragments, do not occur if selectively double-labeled are used instead of single-labeled peptides.

In a preferred embodiment the methods and substances of the present invention are applied to the quantification of human plasma proteins (FIG. 11, FIG. 12). In a first step proteins are extracted from a plasma sample and solubilized. The proteins are then subjected to reduction and alkylation, prior to cleavage into peptides, preferably using a protease, typically trypsin and/or Lys-C. The digested endogenous, unlabeled peptides are then pooled with synthetic, selectively double-labeled reference peptides. The peptide mixture is desalted, typically using C18 stationary phase. Peptides are separated via liquid chromatography, typically by increasing hydrophobicity via a reversed-phase column and a gradient of increasing acetonitrile concentrations. Peptides elute, are ionized and subjected to MS analysis via either a DIA—(FIG. 11) or an mPRM-method (FIG. 12). Fragment ions are detected on a high resolution instrument and combined fragment ion spectra containing several precursors are stored. Since the reference peptides contain two strategically positioned labels, most of their fragments will be labeled. Thus, most corresponding fragment ions from unlabeled endogenous and labeled reference peptides will have distinct masses and fragment overlap between peptides is greatly reduced. Based on MS2 data peptides and/or proteins will be identified and quantified using specialized software. Alternatively, other data analysis workflows mentioned in the text can be employed, e.g. quantification based on MS1 level data. Using this workflow the endogenous, unlabeled peptides can be quantified relative to the labeled reference peptides. If the concentration of the labeled reference peptides within the sample is known, this further enables absolute quantification of the unlabeled peptides. Proteins are then quantified based on the amount of their peptides. In a second aspect, we analyzed the fragment overlap occurring during DIA- and mPRM-based quantification of human plasma peptides and/or proteins with sets of single-labeled and double-labeled synthetic peptides (FIGS. 11-16). FIGS. 13, and 15 show mPRM and DIA data, respectively, for peptide DIASGLIGPLIIC[+C2+H3+N+O]K present in an unlabeled, as well as a labeled variant carrying a modified lysine residue (K8) as single C-terminal label. Precursors of both peptide variants were fragmented and a combined fragment ion spectrum comprising fragment ions from both the unlabeled and the labeled peptide was stored. Using analysis software, we compared fragment ion signals attributed to the unlabeled and the labeled peptide (FIGS. 13a, 15a). The fragment overlap was analyzed. Fragment ions from the unlabeled (light) precursor are marked with white triangles, fragment ions from the labeled (heavy) precursor are marked with black triangles, and shared b-ions are marked with pointed circles. A mass shift between corresponding fragment ions from unlabeled and labeled peptides due to the C-terminal and/or N-terminal label is displayed as a line connecting two triangles. Symbols (* or #) mark mass shifts due to the C-terminal, or the N-terminal label, respectively. All y-ions show a mass shift. On the other hand, fragment overlap was observed for all b-ions in the spectrum. This affects the relative fragment ion intensities which differ between the respective peptide variants (FIGS. 13b, 15b). Moreover, it affects quantification: The y-ions show unlabeled-to-labeled intensity ratios from 0.11 to 0.18 which reflects the ratio between the light and heavy precursor (FIGS. 13c, 15c). However, if b-ions are to be used for quantification, they show an L/H ratio of 1 since the same shared fragment ion peaks are compared between light and heavy peptides. Thus, if the b-ions are considered in the calculation they will skew the L/H ratios towards a higher amount of unlabeled peptide. On the other hand, if all b-ions are ignored, the quantification is less robust compared a case where all fragments correctly represent the ratios between unlabeled and labeled precursors present in the sample. All these problems, fragment overlap leading to inaccurate quantitative values or unused ions and shared fragments, do not occur if selectively double-labeled peptides are used instead of single-labeled peptides.

Figure 14:
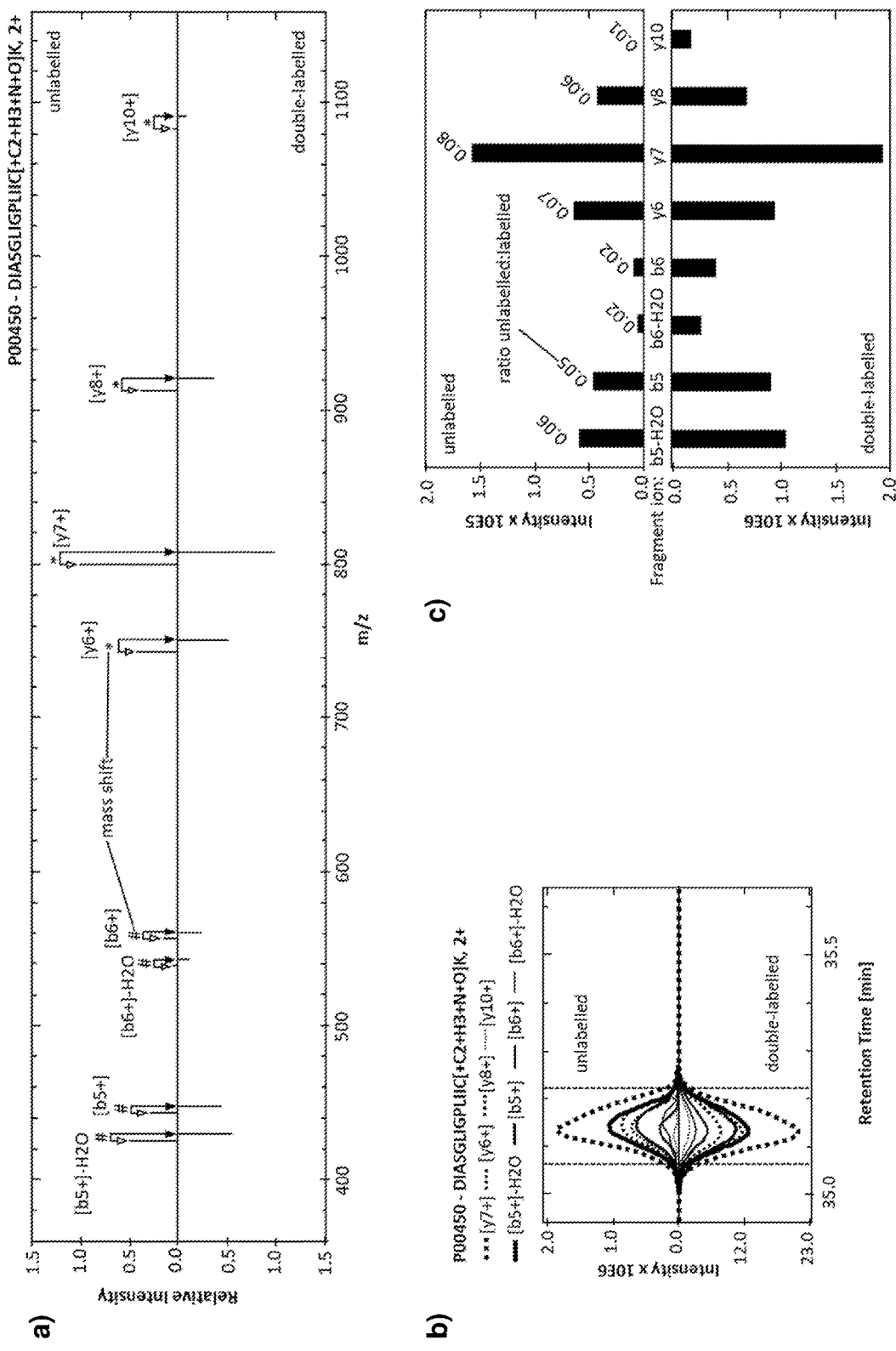
FIG. 14 shows a) a combined fragment ion spectrum acquired with mPRM comprising fragment ions from the unlabeled and the double heavy-labeled variant of peptide DIASGLIGPLIIC[+C2+H3+N+O]K, b) the fragment ion traces for fragment ions from the unlabeled and the double heavy-labeled variant of peptide DIASGLIGPLIIC[+C2+H3+N+O]K, and c) a barplot depicting fragment-ion intensities for the unlabeled and the double heavy-labeled variant of peptide DIASGLIGPLIIC[+C2+H3+N+O]K and the fragment ion intensity ratio between the two variants. The code [+C2+H3+N+O] denotes a carbamidomethyl modification at cysteine that is typically introduced on purpose during sample preparation.

FIGS. 14 (mPRM data) and 16 (DIA data) show the corresponding plots for the unlabeled and the double labeled variants of the peptide. Both b- and y-ions show no fragment overlap (FIG. 14a, FIG. 16a). Both peptide variants produce similar relative fragment ion intensities (FIG. 14b, FIG. 16b). Moreover, b- and y-ions show similar unlabeled-to-labeled intensity ratios which reflect the ratio between the light and heavy precursor (FIGS. 14c, 16c).

Figure 17:
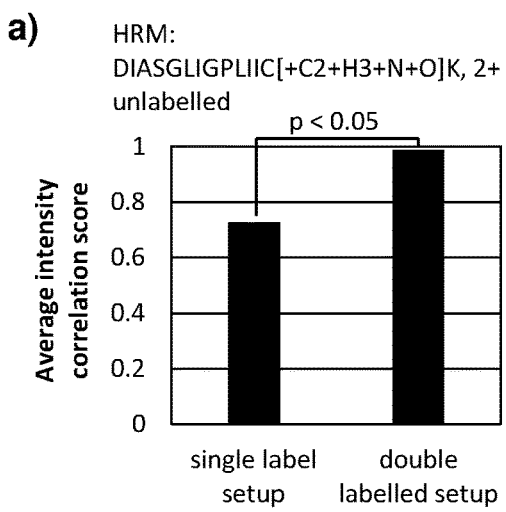
FIG. 17 shows a) a barplot depicting the intensity correlation score (average over 3 replicates) for the unlabeled variant of peptide DIASGLIGPLIIC[+C2+H3+N+O]K in an experimental setup using DIA and using reference peptides with a single C-terminal label, or double-labeled reference peptides. The code [+C2+H3+N+O] denotes a carbamidomethyl modification at cysteine that is typically introduced on purpose during sample preparation. b) a barplot depicting the average intensity correlation score (over 3 replicates and 5 peptides) for the unlabeled variants of 5 peptides in an experimental setup using DIA and using reference peptides with a single C-terminal label, or double-labeled reference peptides.
Figure 17:
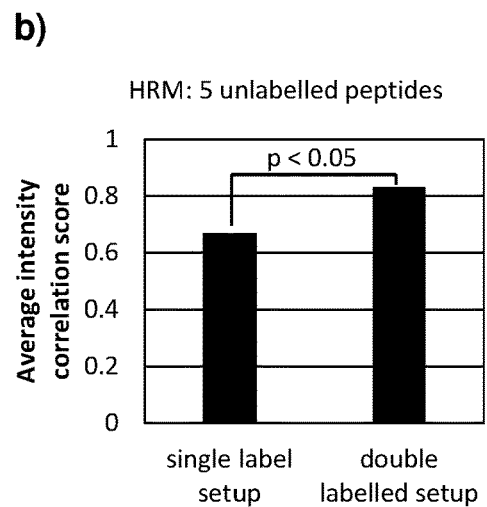

Moreover, we re-analyzed data from the DIA experiments described above (FIG. 15, FIG. 16) to test if using single-labeled reference peptides negatively influenced the identification of the unlabeled peptides. In our setup the reference peptides was present in higher amounts than the endogenous, unlabeled peptides. If a reference peptide with a single C-terminal label is used, some of its fragment ions overlap with fragment ions of the less abundant, unlabeled peptide. Therefore, the relative fragment ion intensities were mainly skewed for the less abundant, unlabeled peptide (FIG. 15). We analyzed the impact of these skewed relative fragment intensities on the peptide identification score. To this end we analyzed Spectronaut's intensity correlation score. The intensity correlation score takes into account the expected relative fragment ion intensities based on the spectral library and the fit with the actual relative fragment intensities of the measured peak. It is used for scoring of peptide and peak identification and thus is a good measure for how much altered relative fragment intensities by fragment overlap will affect peptide and/or protein identification. We analyzed the intensity correlation score for five peptides measured in the DIA experiments described above (FIGS. 15, 16, 17). FIG. 17a shows data from the DIA experiment and depicts the intensity correlation score for the unlabeled peptide DIASGLIGPLIIC[+C2+H3+N+O]K averaged over 3 replicates. If double-labeled reference peptides were used, the average intensity correlation score was significantly higher than when reference peptides with a single C-terminal label were used (t-test, $p<0.05$). This also held true for other peptides. The average intensity correlation score for 5 unlabeled peptides was significantly higher in an experimental setup using double-labeled reference peptides compared to reference peptides with a single C-terminal label (FIG. 17b).

Experimental Part:

EXAMPLE 1

Quantification of Human Plasma Proteins Using Selectively Double-Labeled Peptides See FIG. 11 for a scheme of the workflow.

Sample Preparation:

Human plasma will be digested using in solution digestion: 10 µl of plasma will be diluted in 75 µl 10 M urea and 0.1 M ammonium bicarbonate. The samples will be reduced with 5 mM TCEP for 1 h at 37° C. Subsequently, the plasma will be alkylated with 25 mM iodoacetamide for 20 min at 21° C. The samples will be diluted to 2 M urea and digested with trypsin at a ratio 1:100 (enzyme to protein) at 37° C. for 15 h. The samples will be centrifuged at 20,000 g at 4° C. for 10 min. The peptides will be desalted using C18 MacroSpin columns from The Nest Group according to the manufacturer's instructions. After drying, the peptides will be resuspended in 1% ACN and 0.1% formic acid.

Preparation of Labeled Reference Peptides:

The reference peptide mix will contain synthetic double-labeled peptides covering amino acid sequences of interest, the unlabeled, endogenous version of which will be quantified within the samples. These dried, labeled reference peptides will be dissolved in 20 µl dissolution buffer before adding 100 µl of LC solution to it. Dissolution will be assisted by vortexing and/or sonication. Two microliters of this reference peptide mix will be added to each sample.

Mass Spectrometry Analysis:

Two micrograms of each sample will be analyzed using a self-made analytical column (75 µm×50 cm length, packed with ReproSil-Pur 120 A C18-AQ, 1.9 µm) at 50° C. on an Easy-nLC 1200 connected to a Q Exactive HF mass spectrometer (Thermo Scientific). The peptides will be separated by a 1 h segmented gradient from 1 to 52% ACN in 60 min with 0.1% formic acid at 250 nl/min, followed by a linear increase to 90% ACN in 2 min and 90% for 10 min. The DIA-MS method will consist of a survey scan at 120,000 resolution from 350 to 1,650 m/z (AGC target of $3*10^6$ or 60 ms injection time). Then, 14 DIA windows will be acquired at 30,000 resolution (AGC target $3*10^6$ and auto for injection time) spanning 350-1650 m/z. Stepped collision energy will be 10% at 27%. The spectra will be recorded in profile mode. The default charge state for the MS2 will be set to 4.

Data Analysis:

Peptide and protein identification, as well as quantification will be done using any suitable software, such as for example Spectronaut, OpenSWATH, SpectroDive or MaxQuant.

EXAMPLE 3

Method for Selecting Cheapest Amino Acid for Labeling and Estimate Total Label Costs A method was created to select optimal amino acids and positions for labeling. Furthermore, the method estimated the total label cost for double-labeling a set of peptides. It offered the following features:

In a first step three pieces of input data were accepted, the first containing the label prices, i.e. the price of amino acids containing heavy elemental isotopes as stated by a certain vendor, the second containing the molecular weight of all 20 amino acids, and the third being a spectral library for human plasma.

In a second step the label prices and the amino acid molecular weight data was used to estimate the cost per mmol of each labeled amino acid. Furthermore, all unique, unmodified peptide sequences were extracted from the spectral library.

In a third step a value for $n_{globalMaxVal}$ was specified. Herein $n_{globalMaxVal}$ defines a positive integer that is set by the experimenter, e.g. $n_{globalMaxVal}=4$. The highest possible value for $n_{globalMaxVal}$ is equal to the length of the longest peptide in the analyzed peptide spectral library divided by two, and rounded down to the nearest lower positive integer if the value was not an integer.

In a fourth step, the value for $n_{globalMaxVal}$, the values for label cost per mmol, and the peptide sequences from the spectral library were used to select the cheapest amino acid for labeling, to estimate the total label cost, and to calculate the frequency with which each amino acid was labeled for the set of peptides for different $n_{globalMaxVal}$ values. For each peptide stretches of $n_i$ amino acids from each terminus were considered. The $n_i$ values were peptide-specific and related to an amino acid stretch starting from the terminus of a peptide, e.g. a value of $n_i=1$ comprised the terminal amino acid, $n_i=2$ comprised the terminal amino acid and the amino acid one removed from the terminus, and so forth. The cheapest amino acid and the total label costs were determined as follows:

For each peptide sequence extracted from the library the peptide-specific value for $n_i$ was equal to the lower of two values: either the value of the user-defined positive integer $n_{globalMaxVal}$, or the value of $n_{pepMaxVal}$ which corresponds to the number of amino acids in the peptide divided by two and rounded down to the nearest lower integer if the value was not an integer. The position and the cost of the first label for said peptide were determined by selecting the amino acid with the lowest label cost per millimole from a stretch of amino acids of length $n_i$ starting from the C-terminus. The position and the cost of the second label were determined by applying the same procedure to the N-terminus. This was repeated for all peptide sequences. The label costs for all peptide sequences were summed up to obtain the total label cost for the selected $n_{globalMaxVal}$ value.

This calculation was repeated for different integer values of $n_{globalMaxVal}$ between 1 and the maximum possible value of $n_{globalMaxVal}$ (length of longest peptide in the library divided by two and rounded down to the next lowest integer). As a result, a separate total label cost was calculated for each $n_{globalMaxVal}$ value.

In a fifth step, the resulting total label costs for labeling the peptide sequences were displayed for each $n_{globalMaxVal}$ value. Furthermore, the frequencies with which each of the 20 amino acids had been selected for labeling, were calculated (FIG. 8).

EXAMPLE 4

Exclusion of Modified Amino Acids and Analysis of Fragment Collisions

A method for the selection of labels and label positions will be created which will offer the following features in addition to the label cost calculation features of Example 3:

After the optimization of label positions according to total label cost as in Example 3, the present method will in a first aspect select the amino acid with the next lowest label cost for labeling if the selected amino acid is an amino acid that is often post-translationally modified in the experimental setup. In a second aspect the method will simulate the fragment masses that would be produced by the selected double-labeled peptide sequences. Based on the simulation the method will further analyze how many fragment collisions occur, i.e. how many fragment ions from the double-labeled precursor overlap with any other fragment ions of the unlabeled precursor. If the number lies above a certain threshold, the amino acid with the next lowest label cost with a number of fragment collisions which lies below the threshold will instead be selected for labeling if such a residue is available.

EXAMPLE 5

Set of Synthetic Double-Labeled Human Plasma Peptides

A list of tryptic sequences extracted from a human plasma spectral library will be analyzed. The value for $n_{globalMaxVal}$ will be set equal to 4. For each peptide stretches of $n_i$ amino acids from each terminus were considered. The $n_i$ values will be peptide-specific and relate to an amino acid stretch starting from the terminus of a peptide, e.g. a value of $n_i=1$ comprises the terminal amino acid, $n_i=2$ comprises the terminal amino acid and the amino acid one removed from the terminus, and so forth.

For each peptide sequence extracted from the library the peptide-specific value for $n_i$ will be equal to the lower of two values: either the value of the user-defined positive integer $n_{globalMaxVal}$, or the value of $n_{pepMaxVal}$ which corresponds to the number of amino acids in the peptide divided by two and rounded down to the nearest lower integer if the value was not an integer.

For each peptide a first amino acid having the lowest label cost from the $n_i$ most C-terminal amino acids, and a second amino acid having the lowest label cost from the $n_i$ most N-terminal amino acids will be selected for labeling. $n_i$ will adopt values 1, 2, 3, and 4 for different peptides, depending on their length, e.g. for a peptide of six amino acids $n_i$ will be 3, for a peptide of seven amino acids $n_i$ will be 3, for a peptide of eight amino acids, $n_i$ will be 4.

The most appropriate 1, 2, 3, 4, 5 or more peptides per protein will be selected based on labeling cost and other criteria (such as peptide length, hydrophobicity and so forth). Furthermore, total label costs for $n_{globalMaxVal}$ will be estimated. Special selection criteria will apply in case fragment collisions occur or in case the selected amino acid is easily modified. The corresponding set of quantified, double-labeled peptides corresponding to the data of $n_{global-MaxVal}=4$ will be synthesized wherein the labels are the designated amino acids containing $^{13}C$ and/or $^{15}N$.

The set of synthetic double-labeled peptides will be diluted appropriately. A suitable amount of the double-labeled peptide mix will be added to a sample containing an unlabeled protein digest from human plasma. Fragment ion spectra for the combined peptide mixture will be acquired using a DIA method. Due to the labeled peptides being added in known amounts, absolute peptide abundances in the unlabeled sample can then be determined using specialized software. Due to the synthetic peptides containing two labels, their b- and y-ions series will have different masses from the corresponding ions of the unlabeled peptide. Thus, no fragment overlap will occur.

EXAMPLE 6

Quantification of Human Plasma Peptides Using Selectively Double-Labeled Peptides See FIGS. 11 and 12 for a scheme of the workflow using DIA and mPRM methods, respectively. See FIGS. 13, 14 and FIGS. 15, 16, 17 for results from mPRM and DIA workflows, respectively.

Sample Preparation:

Human plasma sample was prepared by in solution digestion: 10 µl of plasma was diluted in 90 µl 10 M urea in 0.1 M ammonium bicarbonate. The sample was reduced with 5 mM dithiothreitol for 30 minutes at 37° C. Subsequently, the plasma was alkylated with 27 mM iodoacetamide for 30 minutes at 21° C. protected from light. The sample was diluted to a urea concentration below 1.5 M and digested with trypsin at a ratio 1:50 (enzyme to protein) at 37° C. for 3 hours. The sample was centrifuged at 14,000×g at 4° C. for 15 minutes, before the peptides were desalted using a C18 MacroSpin 96-well plate (The Nest Group) according to the manufacturer's instructions. After complete drying in a vacuum concentrator, the plasma sample was re-suspended in 1% ACN and 0.1% formic acid and frozen at −20° C. until further use.

Preparation of Labeled Reference Peptides:

The reference peptide mix contained five synthetic, double-labeled peptides covering amino acid sequences of interest, the unlabeled, endogenous version of which will be quantified within the samples.

Stock solutions of the individual peptides and a working solution of the reference peptide mix were prepared according to the following table:

Of the working solution 2 µl was added to 6 µl of plasma sample. Additionally, 0.8 µl of iRT peptides were added to the sample before injection. Purity of the double labeled peptides, concerning single or non-labeled contaminates, was confirmed by mass-spectrometric analysis (data not shown).

As comparison for single labeled reference peptides, Biognosys' PlasmaDive reference peptide mix was used, according to the manufacturer's instructions. The mix comprises the sequences of the five double-labeled peptides in their single-labeled variant, i.e. with a single C-terminal heavy amino acid.

Mass Spectrometry Analysis:

One microgram of each sample was analyzed using a self-made analytical column (75 µm×50 cm length, packed with ReproSil-Pur 120 A C18-AQ, 1.9 µm) at 50° C. on an Easy-nLC 1200 connected to a Q Exactive HF mass spectrometer (Thermo Scientific). The peptides were separated by a 40 minutes (PRM) linear gradient or 60 minutes segmented gradient (DIA) from 1 to 45% ACN with 0.1% formic acid at 250 nl/min. The DIA-MS method consisted of a survey scan at 120,000 resolution from 350 to 1,650 m/z (AGC target of $3*10^6$ or 60 ms injection time). Then, 14 DIA windows were acquired at 30,000 resolution (AGC target $3*10^6$ and auto for injection time) spanning 350-1650 m/z. Normalized stepped collision energy from 10% to 27% was used and the spectra were recorded in profile mode. The default charge state for the MS2 was set to 3. For the PRM analysis, the settings were similar, but only the five heavy labeled peptides and endogenous counterparts were targeted, as well as iRT peptides. The instrument was set to use multiplexing and analyze heavy-light pairs together.

Data Analysis:

The multiplexed PRM files were analyzed with SpectroDive 7 (Biognosys) and the DIA runs with Spectronaut 9 (Biognosys), both using standard settings, according to the manufacturer's instructions.

LIST OF REFERENCE SIGNS/ABBREVIATIONS

CID collision-induced dissociation
ECD electron-capture dissociation
ESI electrospray ionization
ETD electron-transfer dissociation
HCD Higher-energy collisional dissociation
LC liquid chromatography
MALDI matrix-assisted laser desorption ionization
mmol millimole
mPRM multiplexed parallel reaction monitoring
MS mass spectrometry
m/z mass to charge ratio
NETD negative electron transfer dissociation

| Peptide | Stock Solution (fmol/µl) | Stock Solution (µl) | Dilution | Working Solution (fmol/µl) |
|---|---|---|---|---|
| _PVA*FSVVPTAAAAVSLK*_ | 670776.7 | 1000 | 404.4 | 1658.6 |
| _AG*LLRPDYALLGHR*_ | 702996.7 | 1000 | 1209.8 | 581.1 |
| _DIA*SGLIGPLIIC[+C2+H3+N+O]K*_ | 742360.4 | 1000 | 583.9 | 1271.3 |
| _G*LTLHLK*_ | 1389099.4 | 1000 | 2271.7 | 611.5 |
| _EHV*AHLLFLR*_ | 879725.5 | 1000 | 276.7 | 3179.3 |

Heavy labeled amino acids are marked by a star (*) following the amino acid letter.

PQD Pulsed Q Collision Induced Dissociation
SRM selected reaction monitoring

The invention claimed is:

1. A method for the absolute or relative quantitative analysis of proteins and/or peptides with or without post translational modification(s) using a mass spectrometry method in which:
  in a first step unlabeled proteins from an endogenous mixture are digested and subsequently digestion products thereof selected,
  in a second step said digestion products are fragmented, and
  in a third step a combined fragment spectrum is acquired comprising b-ions and y-ions of said digestion products,
  wherein at least one reference peptide is added to said mixture before and/or after digestion, is fragmented, acquired, and stored in said combined fragment spectrum comprising also b-ions and y-ions of said digestion products,
  wherein the said at least one reference peptide is added in a known concentration for absolute quantification or in always the same concentration in a series of experiments for relative quantitative analysis,
  wherein said at least one reference peptide this is selectively isotopically labeled by having incorporated:
    one isotopically labeled amino acid forming its very C-terminus or being one of the four terminal amino acids at the C-terminus and
    one isotopically labeled amino acid forming its very N-terminus, or being one of the four terminal amino acids at the N-terminus, and
  wherein the isotopically labeled amino acids are unmodified naturally occurring proteinogenic amino acids or amino acids carrying a chemically modifying moiety, wherein said unmodified naturally occurring proteinogenic amino acids or amino acids carrying a chemically modifying moiety comprise one or more atoms that are isotopically labeled such that said one or more atoms are present in the amino acid and not in the chemically modifying moiety.

2. The method according to claim 1, wherein in said reference peptide, apart from the isotopically labeled amino acid at or close to the C-terminus and the isotopically labeled amino acid at or close to the N-terminus, not more than one additional amino acid is isotopically labeled.

3. The method according to claim 1, wherein in said reference peptide one isotopically labeled amino acid is forming its very C-terminus and one further isotopically labeled amino acid is forming its very N-terminus.

4. The method according to claim 1, wherein said combined fragment spectrum is acquired using a mass isolation window having a full-range mass isolation window, or a width in terms of mass-to-charge ratio in the range of $(2 \times 1.036426 \times 10^{-8}$ kg/C$)$–$(1000 \times 1.036426 \times 10^{-8}$ kg/C$)$.

5. The method according to claim 1, wherein said combined fragment spectrum is acquired using a mass isolation window of $(5 \times 1.036426 \times 10^{-8}$ kg/C$)$–$(30 \times 1.036426 \times 10^{-8}$ kg/C$)$.

6. The method according to claim 1, wherein said post translational modification is one or more selected from the group consisting of: phosphorylation, acetylation, methylation, sulfation, hydroxylation, lipidation, ubiquitylation, sumoylation, and glycosylation.

7. The method according to claim 1, wherein said reference peptide consists of 5-100 amino acids.

8. The method according to claim 1, wherein it involves using DIA or mPRM techniques.

9. The method according to claim 1, wherein in said reference peptide, apart from the isotopically labeled amino acid at or close to the C-terminus and the isotopically labeled amino acid at or close to the N-terminus, no additional amino acid is isotopically labeled.

10. The method according to claim 1, wherein said combined fragment spectrum is acquired using a mass isolation window having a full-range mass isolation window, or a width in terms of mass-to-charge ratio in the range of $(5 \times 1.036426 \times 10^{-8}$ kg/C$)$–$(100 \times 1.036426 \times 10^{-8}$ kg/C$)$.

11. The method according to claim 1, wherein said combined fragment spectrum is acquired using a mass isolation window of $(10 \times 1.036426 \times 10^{-8}$ kg/C$)$–$(25 \times 1.036426 \times 10^{-8}$ kg/C$)$.

12. The method according to claim 1, wherein said reference peptide consists of 7-30 amino acids.

13. The method according to claim 1, wherein said reference peptide consists of 10-20 amino acids.

* * * * *